(12) United States Patent
Meyers

(10) Patent No.: US 7,094,565 B1
(45) Date of Patent: Aug. 22, 2006

(54) 21612, NOVEL HUMAN DEHYDROGENASES

(75) Inventor: Rachel Meyers, Newton, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 626 days.

(21) Appl. No.: 09/464,039

(22) Filed: Dec. 15, 1999

(51) Int. Cl.
*C12P 21/06* (2006.01)
*C12N 5/00* (2006.01)
*C12N 15/00* (2006.01)
*C12N 15/63* (2006.01)
*C07H 21/02* (2006.01)
*C07H 21/04* (2006.01)
*C07K 1/00* (2006.01)

(52) U.S. Cl. ............... 435/69.1; 435/320.1; 435/325; 435/455; 536/23.1; 536/23.5; 530/350

(58) Field of Classification Search ............... 435/69.1, 435/320.1, 325, 455; 536/23.1, 23.5; 530/350
See application file for complete search history.

(56) References Cited

PUBLICATIONS

Duester et al., Families of retinoid dehydrogenases regulating vitamin A function production of visual pigment and retinoic acid, 2000, Eur. J. Biochem, vol. 267, pp. 4315–4324.*
Rosenberg et al., Gene therapist, Heal thyself, 2000, SCIENCE, vol. 287, p. 1751.*
Wood, Phenotype Assessment: Are you Missing Something?, 2000, Comparative Medicine, vol. 50, pp. 12–15.*
AA622988/c, NCI–CGAP http://www.ncbi.nlm.nih.gov/ncicgap, Oct. 1997.*
Krozowski, Z., "The Short–chain Alcohol Dehydrogenase Superfamily: Variations on a Common Theme," *J. Steroid Biochem. Molec. Biol.*, 1994, pp. 125–130, vol. 51.
Yoshida, et al., "Genetics of Human Alcohol–Metabolizing Enzymes," *Progress in Nucleic Acid Research and Molecular Biology*, 1991, pp. 255–287, vol. 40.
EMBL Database for Accession No. AC003042, Nov. 5, 1997 (XP002173560).
EMBL Database for Accession No. Q9XYN2, Nov. 1, 1992 (XP002173561).
EMBL Database for Accession No. O34187, Jan. 1, 1998 (XP002173562).
EMBL Database for Accession No. O25124, Jan. 1, 1998 (XP002173563).
Blast searches of clone 21615 against the following databases: NRN/nuc; NRP/protxnu; patent 2/gsprot; Patent DbPreviewNuc; patent 2/gsnuc; DBEST/dbEST.
Blast searches of clone 21676 against the following databases: db/NRN/nuc; DBEST/dbEST; Patent 2/Patent DbPreviewNuc; and Patent 2/gsnuc.
Blast searches of clone 21612 against the following datagases: DBEST/dbEST; db/NRN/nuc; PatentDbPreviewNuc; Patent 2/gsnuc; Patent 2/gsprot; NRP/protot.
Clustal W (V 1.74) pairwise sequence alignment of clone 21612.
Blast searches for clone 21620 against the folowing databases: DBEST/dbEST; NRN/nuc; Patent 2/Patent DbPreviewNuc; Patent 2/gsnuc; Patent 2/gsprot; NRP/protot; and NRP/protxnu.
Clustal W (V 1.74) pairwise alignment of clone 21620.
Blast searches of clone 33756 against the following databases: DBEST/dbEST; NRN/nuc; Patent 2/Patent DbPreviewNuc; Patent 2/gsnuc; Patent 2/gsprot; NRP/protot; NRP/protxnu.
Clustal W (V 1.74) pairwise alignment of clone 33756.

* cited by examiner

*Primary Examiner*—Jeffrey Fredman
*Assistant Examiner*—Sumesh Kaushal
(74) Attorney, Agent, or Firm—Millennium Pharmaceuticals, Inc.

(57) ABSTRACT

The present invention relates to newly identified human ADHs belonging to the superfamily of mammalian alcohol dehydrogenases. The invention also relates to polynucleotides encoding the ADHs. The invention further relates to methods using the ADH polypeptides and polynucleotides as a target for diagnosis and treatment in ADH-mediated or -related disorders. The invention further relates to drug-screening methods using the ADH polypeptides and polynucleotides to identify agonists and antagonists for diagnosis and treatment. The invention further encompasses agonists and antagonists based on the ADH polypeptides and polynucleotides. The invention further relates to procedures for producing the ADH polypeptides and polynucleotides.

26 Claims, 26 Drawing Sheets

```
Input file Fbh21620fl.seq; Output File 21620.trans
Sequence length 1909

TACTTAGACTCAGCCGGCTTTTCCACGCTTTGCCTGACCCTGCTTTGCTCAACTGTACGTCTTGTTTCGTTTTCTGTTC

TGCGCCGTTACAGATCCAAGCTCTGAAAAACCAGAAAGTTAACTGGTAAGTTTAGTCTTTTTGTCTTTTATTTCAGGTC

CCGGATCCGGTGATCCAAATCTAAGAACTGCTCCTCAGTGAGTGTTGCCTTTACTTCTAGGCCTGTACGGAAGTGTTAC

TTCTGCTCTAAAAGCTGCGGAATTCTAATACGACTCACTATAGGGAGTCGACCCACGCGTCCGGGGTCTAGGCGCGGAT

CGGACCCAAGCAGGTCGGCGGCGGCGGCAGGAGAGCGGCCGGGCGTCAGCTCCTCGACCCCCGTGTCGGGCTAGTCCAG

M   A   R   P   G   M   E   R   W   R   D   R   L    13
CGAGGCGGACGGGCGGCGTGGGCCC ATG GCC AGG CCC GGC ATG GAG CGG TGG CGC GAC CGG CTG    39

A   L   V   T   G   A   S   G   G   I   G   A   A   V   A   R   A   L   V   Q    33
GCG CTG GTG ACG GGG GCC TCG GGG GGC ATC GGC GCG GCC GTG GCC CGG GCC CTG GTC CAG    99

Q   G   L   K   V   V   G   C   A   R   T   V   G   N   I   E   E   L   A   A    53
CAG GGA CTG AAG GTG GTG GGC TGC GCC CGC ACT GTG GGC AAC ATC GAG GAG CTG GCT GCT   159

E   C   K   S   A   G   Y   P   G   T   L   I   P   Y   R   C   D   L   S   N    73
GAA TGT AAG AGT GCA GGC TAC CCC GGG ACT TTG ATC CCC TAC AGA TGT GAC CTA TCA AAT   219

E   E   D   I   L   S   M   F   S   A   I   R   S   Q   H   S   G   V   D   I    93
GAA GAG GAC ATC CTC TCC ATG TTC TCA GCT ATC CGT TCT CAG CAC AGC GGT GTA GAC ATC   279

C   I   N   N   A   G   L   A   R   P   D   T   L   L   S   G   S   T   S   G   113
TGC ATC AAC AAT GCT GGC TTG GCC CGG CCT GAC ACC CTG CTC TCA GGC AGC ACC AGT GGT   339

W   K   D   M   F   N   V   N   V   L   A   L   S   I   C   T   R   E   A   Y   133
TGG AAG GAC ATG TTC AAT GTG AAC GTG CTG GCC CTC AGC ATC TGC ACA CGG GAA GCC TAC   399

Q   S   M   K   E   R   N   V   D   D   G   H   I   I   N   I   N   S   M   S   153
CAG TCC ATG AAG GAG CGG AAT GTG GAC GAT GGG CAC ATC ATT AAC ATC AAT AGC ATG TCT   459

G   H   R   V   L   P   L   S   V   T   H   F   Y   S   A   T   K   Y   A   V   173
GGC CAC CGA GTG TTA CCC CTG TCT GTG ACC CAC TTC TAT AGT GCC ACC AAG TAT GCC GTC   519

T   A   L   T   E   G   L   R   Q   E   L   R   E   A   Q   T   H   I   R   A   193
ACT GCG CTG ACA GAG GGA CTG AGG CAA GAG CTT CGG GAG GCC CAG ACC CAC ATC CGA GCC   579

T   C   I   S   P   G   V   V   E   T   Q   F   A   F   K   L   H   D   K   D   213
ACG TGC ATC TCT CCA GGT GTG GTG GAG ACA CAA TTC GCC TTC AAA CTC CAC GAC AAG GAC   639

P   E   K   A   A   A   T   Y   E   Q   M   K   C   L   K   P   E   D   V   A   233
CCT GAG AAG GCA GCT GCC ACC TAT GAG CAA ATG AAG TGT CTC AAA CCC GAG GAT GTG GCC   699

E   A   V   I   Y   V   L   S   T   P   A   H   I   Q   I   G   D   I   Q   M   253
GAG GCT GTT ATC TAC GTC CTC AGC ACT CCC GCA CAC ATC CAG ATT GGA GAC ATC CAG ATG   759

R   P   T   E   Q   V   T   *                                                   261
AGG CCC ACG GAG CAG GTG ACC TAG                                                  783

TGACTGTGGGAGCTCCTCCTTCCCTCCCCACCCTTCATGGCTTGCCTCCTGCCTCTGGATTTTAGGTGTTGATTTCTGG

ATCACGGGATACCACTTCCTGTCCACACCCCGACCAGGGGCTAGAAAATTTGTTTGAGATTTTTATATCATCTTGTCAA

ATTGCTTCAGTTGTAAATGTGAAAAATGGGCTGGGGAAAGGAGGTGGTGTCCCTAATTGTTTTACTTGTTAACTTGTTC
```

FIGURE 1

TTGTGCCCCTGGGCACTTGGCCTTTGTCTGCTCTCAGTGTCTTCCCTTTGACATGGGAAAGGAGTTGTGGCCAAAATCC

CCATCTTCTTGCACCTCAACGTCTGTGGCTYANGGGCTGGGGTGGCAGAGGGAGGCCTTCACCTTATATCTGTGTTGTT

ATCCAGGGCTCCAGACTTCCTCCTCTGCCTGCCCCACTGCACCCTCTCCCCCTTATCTATCTCCTTCTCGGCTCCCCAG

CCCAGTCTTGGCTTCTTGTCCCCTCCTGGGGTCATCCCTCCACTCTGACTCTGACTATGGCAGCAGAACACCAGGGCCT

GGCCCAGTGGATTTCATGGTGATCATTAAAAAAGAAAAATCGCAACCAAAAAAAAAAAAAAAAAGGGCGGGCCGCTAGAC

TAGTYTAGAGAAAAAACCTCCCACACCTCCCCYBDAMMYTKACGCCGNACGCNANGGGGGCAATCAAGGACGCT

FIGURE 1, Page 2

Back to original.cgi

Analysis of 21620 (260 aa)

Signal Peptide Predictions for 21620

| Method | Predict | Score | Mat@ |
|---|---|---|---|
| SignalP (eukaryote) | NO | | |

Note: amino-terminal 70aa used for signal peptide prediction

Transmembrane Segments Predicted by MEMSAT

| Start | End | Orient | Score |
|---|---|---|---|
| 13 | 32 | ins-->out | 1.3 |

Prosite Pattern Matches for 21620

>PS00005|PDOC00005|PKC_PHOSPHO_SITE Protein kinase C phosphorylation site.

Query: 135    SMK    137

>PS00006|PDOC00006|CK2_PHOSPHO_SITE Casein kinase II phosphorylation site.

Query: 72     SNEE   75
Query: 89     SGVD   92

Analysis of 21620

Query: 135    SMKE   138

>PS00008|PDOC00008|MYRISTYL N-myristoylation site.

Query: 18     GASGGI  23
Query: 24     GAAVAR  29
Query: 40     GCARTV  45
Query: 90     GVDICI  95
Query: 109    GSTSGW  114
Query: 199    GVVETQ  204

>PS00061|PDOC00060|ADH_SHORT Short-chain alcohol dehydrogenase family signature.

Query: 166    YSATKYAVTAL   176

FIGURE 4

```
Input file Fbh33756.seq; Output File 33756.trans
Sequence length 1153

CCGCGCCCCGCCCTCGCAGCCCANNTNCGGACGCGGGCCCAGCCGCGCCTGCGCTTCCGCTCGCCTGTGGCTGCAANNA

GCGCGCTCTTCCTCGGAGCTACCCAGGCGGCTGGTGTAGCAGCAAGCTCCGCGCCGACCCCTGACGCCTGACGCCTGTC

CCCGGCCCGGCATGAGCCGCTACCTGCTGCCGCTGTCGGCGCTGGGCACGGTAGCAGGCGCTCGCCGTGCTGCTCAAGA

M   E   K   C   E   A   A   A   K   D   I   R   G     13
GGCAACATCATCCTGGCCTGCCGAGAC ATG GAG AAG TGT GAG GCG GCA GCA AAG GAC ATC CGC GGG     39

E   T   L   N   H   H   V   N   A   R   H   L   D   L   A   S   L   K   S   I     33
GAG ACC CTC AAT CAC CAT GTC AAC GCC CGG CAC CTG GAC TTG GCT TCC CTC AAG TCT ATC     99

R   E   F   A   A   K   I   I   E   E   E   E   R   V   D   I   L   I   N   N     53
CGA GAG TTT GCA GCA AAG ATC ATT GAA GAG GAG GAG CGA GTG GAC ATT CTA ATC AAC AAC    159

A   G   V   M   R   C   P   H   W   T   T   E   D   G   F   E   M   Q   F   G     73
GCG GGT GTG ATG CGG TGC CCC CAC TGG ACC ACC GAG GAC GGC TTC GAG ATG CAG TTT GGC    219

V   N   H   L   G   H   F   L   L   T   N   L   L   L   D   K   L   K   A   S     93
GTT AAC CAC CTG GGT CAC TTT CTC TTG ACA AAC TTG CTG CTG GAC AAG CTG AAA GCC TCA    279

A   P   S   R   I   I   N   L   S   S   L   A   H   V   A   G   H   I   D   F    113
GCC CCT TCG CGG ATC ATC AAC CTC TCG TCC CTG GCC CAT GTT GCT GGG CAC ATA GAC TTT    339

D   D   L   N   W   Q   T   R   K   Y   N   T   K   A   A   Y   C   Q   S   K    133
GAC GAC TTG AAC TGG CAG ACG AGG AAG TAT AAC ACC AAA GCC GCC TAC TGC CAG AGC AAG    399

L   A   I   V   L   F   T   K   E   L   S   R   R   L   Q   G   S   G   V   T    153
CTC GCC ATC GTC CTC TTC ACC AAG GAG TTG AGC CGG CGG CTG CAA GGC TCT GGT GTG ACT    459

V   N   A   L   H   P   G   V   A   R   T   E   L   G   R   H   T   G   I   H    173
GTC AAC GCC CTG CAC CCC GGC GTG GCC AGG ACA GAG CTG GGC AGA CAC ACG GGC ATC CAT    519

G   S   T   F   S   S   T   T   L   G   P   I   F   W   L   L   V   K   S   P    193
GGC TCC ACC TTC TCC AGC ACC ACA CTC GGG CCC ATC TTC TGG CTG CTG GTC AAG AGC CCC    579

E   L   A   A   Q   P   S   T   Y   L   A   V   A   E   E   L   A   D   V   S    213
GAG CTG GCC GCC CAG CCC AGC ACA TAC CTG GCC GTG GCG GAG GAA CTG GCG GAT GTT TCC    639

G   K   Y   F   D   G   L   K   Q   K   A   P   A   P   E   A   E   D   E   E    233
GGA AAG TAC TTC GAT GGA CTC AAA CAG AAG GCC CCG GCC CCC GAG GCT GAG GAT GAG GAG    699

V   A   R   R   L   W   A   E   S   A   R   L   V   G   L   E   A   P   S   V    253
GTG GCC CGG AGG CTT TGG GCT GAA AGT GCC CGC CTG GTG GGC TTA GAG GCT CCC TCT GTG    759

R   E   Q   P   L   P   R   *                                                     261
AGG GAG CAG CCC CTC CCC AGA TAA                                                    783

CCTCTGGAGCAGATTTGAAAGCCAGGATGGCGCCTCCAGACCGAGGACAGCTGTCCGCCATGCCCGCAGCTTCCTGGCA

CTACCTGAGCCGGGAGACCCAGGACTG
```

FIGURE 7

Back to orfanal.cgi

Analysis of 33756 (260 aa)

Signal Peptide Predictions for 33756

| Method | Predict | Score | Mat@ |
|---|---|---|---|
| SignalP (eukaryote) | NO | | |

Note: amino-terminal 70aa used for signal peptide prediction

No TM domains predicted by MEMSAT for 33756

Prosite Pattern Matches for 33756

>PS00001|PDOC00001|ASN_GLYCOSYLATION N-glycosylation site.

Query:  100     NLSS    103

>PS00005|PDOC00005|PKC_PHOSPHO_SITE Protein kinase C phosphorylation site.

Query:  29      SLK     31
Query:  32      SIR     34
Query:  120     TRK     122
Query:  144     SRR     146
Query:  213     SGK     215
Query:  242     SAR     244
Query:  252     SVR     254

>PS00006|PDOC00006|CK2_PHOSPHO_SITE Casein kinase II phosphorylation site.

Query:  32      SIRE    35
Query:  63      TTED    66
Query:  252     SVRE    255

>PS00008|PDOC00008|MYRISTYL N-myristoylation site.

Query:  149     GSGVTV  154
Query:  160     GVARTE  165
Query:  171     GIHGST  176

FIGURE 10

```
Input file Fbh21676.seq; Output File 21676.trans
Sequence length 1699

GCNTGTGGGTCCCTTCTTNAAATTGGGTCCCCCCGTTTTAGGTAAGTTTAAAAGCTCAAGGTTCAAAGACNGGNCCTTT

TGTCGGGGGCTCCTTGAAGCCTACTAGATCANCGGCTCTCAGCTTTTTTTTTGGGGGNCCCCCCCCTTTGGGAACCCC

CNTGGCTTTGCTTCAAACTTCTAAGGTCTTTTGTTTCGTTTTCTGTTCCTGCGCCGTTACAGATCCAAGYTCTGAAAAA

CCAGAAAGTTAACTGGTAAGTTTAGTCTTTTTGTCTTTTATTTCAGGTCCCGGATCCGGTGGTGGTGCAAATCAAAGAA

CTGCTCCTCAGTGGATGTTGCCTTTACTTCTAGGCCTGTACGAAGTGTTACTTCTGCTCTAAAAGCTGCGGAATTCTAA

TACGACTCACTATAGGGAGTCGACCCACGCGTCCGCGGACGCGTGGGCGGACGCGTGGGCGGAGCTACCCAGGCGGCTG
```

```
                                                                       M   S   R   Y    4
GTGTGCAGCAAGCTCCGCGCCGACTCCGGACGCCTGACGCCTGACGCCTGTCCCCGGCCCGGC ATG AGC CGC TAC   12

L   L   P   L   S   A   L   G   T   V   A   G   A   A   V   L   L   K   D   Y   24
 CTG CTG CCG CTG TCG GCG CTG GGC ACG GTA GCA GGC GCC GCC GTG CTG CTC AAG GAC TAT   72

V   T   G   G   A   C   P   S   K   A   T   I   P   G   K   T   V   I   V   T   44
 GTC ACC GGT GGG GCT TGC CCC AGC AAG GCC ACC ATC CCT GGG AAG ACG GTC ATC GTG ACG  132

G   A   N   T   G   I   G   K   Q   T   A   L   E   L   A   R   R   G   G   N   64
 GGC GCC AAC ACA GGC ATC GGG AAG CAG ACC GCC TTG GAA CTG GCC AGG AGA GGA GGC AAC  192

I   I   L   A   C   R   D   M   E   K   C   E   A   A   A   K   D   I   R   G   84
 ATC ATC CTG GCC TGC CGA GAC ATG GAG AAG TGT GAG GCG GCA GCA AAG GAC ATC CGC GGG  252

E   T   L   N   H   H   V   N   A   R   H   L   D   L   A   S   L   K   S   I  104
 GAG ACC CTC AAT CAC CAT GTC AAC GCC CGG CAC CTG GAC TTG GCT TCC CTC AAG TCT ATC  312

R   E   F   A   A   K   I   I   E   E   E   R   V   D   I   L   I   N   N      124
 CGA GAG TTT GCA GCA AAG ATC ATT GAA GAG GAG GAG CGA GTG GAC ATT CTA ATC AAC AAC  372

A   G   V   M   R   C   P   H   W   T   T   E   D   G   F   E   M   Q   F   G  144
 GCG GGT GTG ATG CGG TGC CCC CAC TGG ACC ACC GAG GAC GGC TTC GAG ATG CAG TTT GGC  432

V   N   H   L   G   H   F   L   L   T   N   L   L   L   D   K   L   K   A   S  164
 GTT AAC CAC CTG GGT CAC TTT CTC TTG ACA AAC TTG CTG CTG GAC AAG CTG AAA GCC TCA  492

A   P   S   R   I   I   N   L   S   S   L   A   H   V   A   G   H   I   D   F  184
 GCC CCT TCG CGG ATC ATC AAC CTC TCG TCC CTG GCC CAT GTT GCT GGG CAC ATA GAC TTT  552

D   D   L   N   W   Q   T   R   K   Y   N   T   K   A   A   Y   C   Q   S   K  204
 GAC GAC TTG AAC TGG CAG ACG AGG AAG TAT AAC ACC AAA GCC GCC TAC TGC CAG AGC AAG  612

L   A   I   V   L   F   T   K   E   L   S   R   R   L   Q   G   S   G   V   T  224
 CTC GCC ATC GTC CTC TTC ACC AAG GAG CTG AGC CGG CGG CTG CAA GGC TCT GGT GTG ACT  672

V   N   A   L   H   P   G   V   A   R   T   E   L   G   R   H   T   G   I   H  244
 GTC AAC GCC CTG CAC CCC GGC GTG GCC AGG ACA GAG CTG GGC AGA CAC ACG GGC ATC CAT  732

G   S   T   F   S   S   T   T   L   G   P   I   F   W   L   L   V   K   S   P  264
 GGC TCC ACC TTC TCC AGC ACC ACA CTC GGG CCC ATC TTC TGG CTG CTG GTC AAG AGC CCC  792

E   L   V   A   Q   P   S   T   Y   L   A   V   A   E   E   L   A   D   V   S  284
 GAG CTG GTC GCC CAG CCC AGC ACA TAC CTG GCC GTG GCG GAG GAA CTG GCG GAT GTT TCC  852

```
GGA AAG TAC TTC GAT GGA CTC AAA CAG AAG GCC CCG GCC CCC GAG GCT GAG GAT GAG GAG    912

V   A   R   R   L   W   A   E   S   A   R   L   V   G   L   E   A   P   S   V    324
GTG GCC CGG AGG CTT TGG GCT GAA AGT GCC CGC CTG GTG GGC TTA GAG GCT CCC TCT GTG    972

R   E   Q   P   L   P   R   *                                                     332
AGG GAG CAG CCC CTC CCC AGA TAA                                                    996

CCTCTGGAGCAGATTTGAAAGCCAGGATGGCGCCTCCAGACCGAGGACAGCTGTCCGCCATGCCCGCAGCTTCCTGGCA

CTACCTGAGCCGGGAGACCCAGGACTGGCGGCCGCTAGACTAGTCTAGAGAAAAAACCTCCCACACCTCCCCCTGAACC

TGAAACAT
```

FIGURE 11, Page 2

21676.prot

Back to original.cgi

Analysis of 21676 (331 aa)

Signal Peptide Predictions for 21676

| Method | Predict | Score | Mat@ |
|---|---|---|---|
| SignalP (eukaryote) | YES |  | 17 |

Note: amino-terminal 70aa used for signal peptide prediction

Transmembrane Segments Predicted by MEMSAT

| Start | End | Orient | Score |
|---|---|---|---|
| 8 | 25 | out-->ins | 0.2 |
| 242 | 261 | ins-->out | 1.5 |

Transmembrane segments for presumed mature peptide

| Start | End | Orient | Score |
|---|---|---|---|
| 226 | 245 | out-->ins | 2.1 |

Prosite Pattern Matches for 21676

>PS00001|PDOC00001|ASN_GLYCOSYLATION N-glycosylation site.

Query: 171    NLSS    174

>PS00005|PDOC00005|PKC_PHOSPHO_SITE Protein kinase C phosphorylation site.

Query: 100    SLK    102
Query: 103    SIR    105
Query: 191    TRK    193
Query: 215    SRR    217
Query: 284    SGK    286
Query: 313    SAR    315
Query: 323    SVR    325

>PS00006|PDOC00006|CK2_PHOSPHO_SITE Casein kinase II phosphorylation site.

Query: 54     TALE   57
Query: 103    SIRE   106
Query: 134    TTED   137
Query: 323    SVRE   326

>PS00008|PDOC00008|MYRISTYL N-myristoylation site.

Query: 12     GTVAGA  17
Query: 28     GACPSK  33
Query: 45     GANTGI  50
Query: 220    GSGVTV  225
Query: 231    GVARTE  236
Query: 242    GIHGST  247

FIGURE 14

```
Input file Fbh21612f11.seq; Output File 21612.trans
Sequence length 2535

AGGCAGAAGTATGCAAAGCATGCATCTCAAATTAGTCAGCAAACCATAGTCCCGGCCCCTAACTCCGCCCATCCCGCCC

CTAACTCCGNCCCAGTTCCGGCCCATTCTCCGCCCCATGGCTGACTAATTTTTTTTATTTATGCAGAGCCGAGGCCGCC

TCGGCCTCTGAGCTATTCCAGAAGTAGTGAGGAGGCTTTTTTGGAGGCCTAGGCTTTTGCAAAAAGCTCCTCGATCGAG

GGGCTCGCATCTCTCCTTCACGCGCCCGCCGCCCTACCTGAGGCCGCCATCCACGCCGGTTGAGTCGCGTTCTGCCGCC

TCCCGCCTGTGGTGCCTCCTGAACTGCGTCCGCCGTCTAGGTAAGTTTAAAGCTCAGGTCGAGACCGGGCCTTTGTCCG

GCGCTCCCTTGGAGCCTACCTAGACTCAGCCGGCTCTCCACGCTTTGCCTGACCCTGCTTGCTCAACTCTACGTCTTTG

TTTCAGTTTTCTGTTCTGCGCCGTTACAGATCCAAGCTCTGAAAAACCAGAAAGTTAACTGGTAAGTTTAGTCTTTTTG

TCTTTTATTTCAGGTCCCGGATCCGGTGGTGGTGCAAATCAAAGAACTGCTCCTCAGTGGATGTTGCCTTTACTTCTAG

GCCTGTACGGAAGTGTTACTTCTGCTCTAAAAGCTGCGGAATTCTAATACGACTCACTATAGGGWGTCGACCCACGCGT
                                                         M   L   P   N   T   G   R     7
CCGCTCGCCGCCGCCGCTGTCGCCGCCACCTCCTCTGATCTACGAAAGTC ATG TTA CCC AAC ACC GGG AGG    21

L   A   G   C   T   V   F   I   T   G   A   S   R   G   I   G   K   A   I   A     27
CTG GCA GGA TGT ACA GTT TTT ATC ACA GGT GCA AGC CGT GGC ATT GGC AAA GCT ATT GCA    81

L   K   A   A   K   D   G   A   N   I   V   I   A   A   K   T   A   Q   P   H     47
TTG AAA GCA GCA AAG GAT GGA GCA AAT ATT GTT ATT GCT GCA AAG ACC GCC CAG CCA CAT   141

P   K   L   L   G   T   I   Y   T   A   A   E   E   I   E   A   V   G   G   K     67
CCA AAA CTT CTA GGC ACA ATC TAT ACT GCT GCT GAA GAA ATT GAA GCA GTT GGA GGA AAG   201

A   L   P   C   I   V   D   V   R   D   E   Q   Q   I   S   A   A   V   E   K     87
GCC TTG CCA TGT ATT GTT GAT GTG AGA GAT GAA CAG CAG ATC AGT GCT GCA GTG GAG AAA   261

A   I   K   K   F   G   G   I   D   I   L   V   N   N   A   S   A   I   S   L    107
GCC ATC AAG AAA TTT GGA GGA ATT GAT ATT CTG GTA AAT AAT GCC AGT GCC ATT AGT TTG   321

T   N   T   L   D   T   P   T   K   R   L   D   L   M   M   N   V   N   T   R    127
ACC AAT ACA TTG GAC ACA CCT ACC AAG AGA TTG GAT CTG ATG ATG AAC GTG AAC ACC AGA   381

G   T   Y   L   A   S   K   A   C   I   P   Y   L   K   K   S   K   V   A   H    147
GGC ACC TAC CTT GCA TCT AAA GCA TGT ATT CCT TAT TTG AAA AAG AGC AAA GTT GCT CAT   441

I   L   N   I   S   P   P   L   N   L   N   P   V   W   F   K   Q   H   C   A    167
ATC CTC AAT ATC AGT CCA CCA CTG AAC CTA AAT CCA GTT TGG TTC AAA CAG CAC TGT GCT   501

Y   T   I   A   K   Y   G   M   S   M   Y   V   L   G   M   A   E   E   F   K    187
TAT ACC ATT GCT AAG TAT GGT ATG TCT ATG TAT GTG CTT GGA ATG GCA GAA GAA TTT AAA   561

G   E   I   A   V   N   A   L   W   P   K   T   A   I   H   T   A   A   M   D    207
GGT GAA ATT GCA GTC AAT GCA TTA TGG CCT AAA ACA GCC ATA CAC ACT GCT GCT ATG GAT   621

M   L   G   G   P   G   I   E   S   Q   C   R   K   V   D   I   I   A   D   A    227
ATG CTG GGA GGA CCT GGT ATC GAA AGC CAG TGT AGA AAA GTT GAT ATC ATT GCA GAT GCA   681

A   Y   S   I   F   Q   K   P   K   S   F   T   G   N   F   V   I   D   E   N    247
GCA TAT TCC ATT TTC CAA AAG CCA AAA AGT TTT ACT GGC AAC TTT GTC ATT GAT GAA AAT   741

```
                ATC TTA AAA GAA GAA GGA ATA GAA AAT TTT GAC GTT TAT GCA ATT AAA CCA GGT CAT CCT   801
  L   Q   P   D   F   F   L   D   E   Y   P   E   A   V   S   K   K   V   E   S   287
TTG CAA CCA GAT TTC TTC TTA GAT GAA TAC CCA GAA GCA GTT AGC AAG AAA GTG GAA TCA   861

T   G   A   V   P   E   F   K   E   E   K   L   Q   L   Q   P   K   P   R   S   307
ACT GGT GCT GTT CCA GAA TTC AAA GAA GAG AAA CTG CAG CTG CAA CCA AAA CCA CGT TCT   921

G   A   V   E   E   T   F   R   I   V   K   D   S   L   S   D   D   V   V   K   327
GGA GCT GTG GAA GAA ACA TTT AGA ATT GTT AAG GAC TCT CTC AGT GAT GAT GTT GTT AAA   981

A   T   Q   A   I   Y   L   F   E   L   S   G   E   D   G   G   T   W   F   L   347
GCC ACT CAA GCA ATC TAT CTG TTT GAA CTC TCC GGT GAA GAT GGT GGC ACG TGG TTT CTT  1041

D   L   K   S   K   G   N   V   G   Y   G   E   P   S   D   Q   A   D   V   367
GAT CTG AAA AGC AAG GGT GGG AAT GTC GGA TAT GGA GAG CCT TCT GAT CAG GCA GAT GTG  1101

V   M   S   M   T   T   D   D   F   V   K   M   F   S   G   K   L   K   P   T   387
GTG ATG AGT ATG ACT ACT GAT GAC TTT GTA AAA ATG TTT TCA GGG AAA CTA AAA CCA ACA  1161

M   A   F   M   S   G   K   L   K   I   K   G   N   M   A   L   A   I   K   L   407
ATG GCA TTC ATG TCA GGG AAA TTG AAG ATT AAA GGT AAC ATG GCC CTA GCA ATC AAA TTG  1221

E   K   L   M   N   Q   M   N   A   R   L   *                                    419
GAG AAG CTA ATG AAT CAG ATG AAT GCC AGA CTG TGA                                  1257
```

AGGAAAATATAAAAAAAAAGTCGACTGCTATGCTCAAAAAGTAAAAAAAGCTCAACAGTTAAAATCTAATGTTTGTTTT

CTTTCCTGTTATATTATAAGGATATGCACGTTTGTTCTGGAAAAGATAGAATTTGTCTCTAAAAGACTTGAAATTGTAA

TTAAAATGGCAAGCTAATCAAACATAAGCTTCATTAAGTGGGATTCTAAGACAGTCTGTGTTTTTATATTTCAAGGGTT

TAACCCTTTGAGCCTTACATCTCATTCACTGTCTTTCTCCAAGAAAAGTATTTTGGGCGGACAGTCAGATCAAGCAGTA

AAATTAGCTCTTTCAAATCTTCTTGTCATGTAAAATGAAGCTAGTCTGTTTTAAAATTTTTAGTTTTGGATTGTATACT

AATGAAAATCTTAATGATGTTTTKRWTTTTTATATACYTAWTTTWAARRAAAWYYTWWWWWRKWCMTTTTWMCAAAAAW

TWTTAAAAAWKRRWWWKWRYTSKGSGMGRASWMWAWRWRAMMC

FIGURE 15, Page 2

21612.prot

Back to orfanal.cgi

Analysis of 21612 (418 aa)

Signal Peptide Predictions for 21612

| Method | Predict | Score | Mat@ |
|---|---|---|---|
| SignalP (eukaryote) | NO | | |

Note: amino-terminal 70aa used for signal peptide prediction

No TM domains predicted by MEMSAT for 21612

Prosite Pattern Matches for 21612

>PS00001|PDOC00001|ASN_GLYCOSYLATION N-glycosylation site.

Query:   101      NASA     104

>PS00005|PDOC00005|PKC_PHOSPHO_SITE Protein kinase C phosphorylation site.

Query:   5        TGR      7
Query:   115      TKR      117
Query:   282      SKK      284
Query:   313      TFR      315
Query:   381      SGK      383
Query:   392      SGK      394

>PS00006|PDOC00006|CK2_PHOSPHO_SITE Casein kinase II phosphorylation site.

Query:   56       TAAE     59
Query:   320      SLSD     323
Query:   338      SGED     341
Query:   372      TTDD     375

>PS00008|PDOC00008|MYRISTYL N-myristoylation site.

Query:   17       GASRGI   22
Query:   52       GTIYTA   57
Query:   128      GTYLAS   133
Query:   353      GGNVGY   358

>PS00342|PDOC00299|MICROBODIES_CTER Microbodies C-terminal targeting signal.

Query:   416      ARL      418

FIGURE 18

> Fbh21615a - Import - complete

```
1     ATGCAAAAGC CGAGNCCGCC TCGGCCTCTA AGCTATTCCA GAAGTAGTAA GAAGGCTTTT
61    TTGAAGGCCT AGGCTTTTGC AAAAAGCTCC TCGATCGAGG GGCTCGCATC TCTCCTTCAC
121   GGGGCCGCCG CCCTACCTGA GGCCGCCATC CACGCCGGTT GAGTCGCGTT CTGCCGCCTC
181   CCGCCTGTGG TGCCTCCTGA ACTGCGTCCG CCGTYTAGGT AAGTTTAAAG CTCAGGTCGA
241   GACCGGGCCT TTGTCCGGCG CTCCCTTGGA GCCTACCTAG ACTCAGCCGG CTCTCCACGC
301   TTTGCCTGAC CCTGCTTGCT CAACTCTACG TCTTTGTTTC GTTTTCTGTT CTGCGCCGTT
361   ACAGATCCAA GCTCTGAAAA ACCAGAAAGT TAACTGGTAA GTTTAGTCTT TTTGTCTTTT
421   ATTTCAGGTC CCGGATCCGG TGGTGGTGCA AATCAAAGAA CTGCTCCTCA GTGGATGTTG
481   CCTTTACTTC TAGGCCTGTA CGGAAGTGTT ACTTCTGCTC TAAAAGCTGC GGAATTCTAA
541   TACGACTCAC TATAGGGAGT CGACCCACGC GTCCGCAAAC CGAGTTCTGG AGAACGCCAT
601   CAGCTCGCTG CTTAAAATTA ACCACAGGT TCCATTATGG GTCGACTTGA TGGGAAAGTC
661   ATCATCCTGA CGGCCGCTGC TCAGGGGATT GGCCAAGCAG CTGCCTTAGC TTTTGCAAGA
721   GAAGGTGCCA AGTCATAGC CACAGACATT AATGAGTCCA AACTTCAGGA ACTGGAAAAG
781   TACCCGGGTA TTCAAACTCG TGTCCTTGAT GTCACAAAGA AGAAACAAAT TGATCAGTTT
841   GCCAATGAAG TTGAGAGACT TGATGTTCTC TTTAATGTTG CTGGTTTTGT CCATCATGGA
901   ACTGTCCTGG ATTGTGAGGA GAAAGACTGG GACTTCTCGA TGAATCTCAA TGTGCGCAGC
961   ATGTACCTGA TGATCAAGGC ATTCCTTCCT AAAATGCTTG CTCAGAAATC TGGCAATATT
1021  ATCAACATGT CTTCTGTGGC TTCCAGCGTC AAAGGAGTTG TGAACAGATG TGTGTACAGC
1081  ACAACCAAGG CAGCCGTGAT TGGCCTCACA AAATCTGTGG CTGCAGATTT CATCCAGCAG
1141  GGCATCAGGT GCAACTGTGT GTGCCCAGGA ACAGTTGATA CGCCATCTCT ACAAGAAAGA
1201  ATACAAGCCA GAGGAAATCC TGAAGAGGCA CGGAATGATT CCTGAAGAG ACAAAAGACG
1261  GGAAGATTCG CAACTGCAGA AGAAATAGCC ATGCTCTGCG TGTATTTGGC TTCTGATGAA
1321  TCTGCTTATG TAACTGGTAA CCCTGTCATC ATTGATGGAG GCTGGAGCTT GTGATTTAG
1381  GATCTCCATG GTGGGAAGGA AGCAGGCCC TTCCTATCCA CAGTGAACCT GGTTACGAAG
1441  AAAACTCACC AATCATCTCC TTCCTGTTAA TCACATGTTA ATGAAAATAA GCTCTTTTTA
1501  ATGATGTCAC TGTTTGCAAG AGTCTGATTC TTTAAGTATA TTAATCTCTT TGTAATCTCT
1561  TCTGAAATCA TTGTAAAGAA ATAAAAATAT TGAACTCAAA AAAAAAAAAA AAAAAGGGC
1621  GGCCGCTAGA CTAGTCTAGA GAAAAAACCT CCCACACCTC CCCCTGAACC TGAAACATAA
1681  AATGAATGCM ATTGTTGKTG GTAACTTGTT ATTGCA
```

FIGURE 19A

> Fbh21615a - Import - complete

MGRDDGKV IILTAAAQGI GQAAALAFAR
EGAKVIATDI NESKLQELEK YPGIQTRVLD VTKKKQIDQF ANEVERLDVL FNVAGFVHHG
TVLDCEEKDW DFSMNLNVRS MYLMIKAFLP KMLAQKSGNI INMSSVASSV KGVVNRCVYS
TTKAAVIGLT KSVAADFIQQ GIRCNCVCPG TVDTPSLQER IQARGNPEEA RNDFLKRQKT
GRFATAEEIA MLCVYLASDE SAYVTGNPVI IDGGWSL*

FIGURE 19B

Back to orfanal.cgi

Analysis of 21615 (245 aa)

Signal Peptide Predictions for 21615

| Method | Predict | Score | Mat@ |
|---|---|---|---|
| SignalP (eukaryote) | NO | | |

Note: amino-terminal 70aa used for signal peptide prediction

Transmembrane Segments Predicted by MEMSAT

| Start | End | Orient | Score |
|---|---|---|---|
| 8 | 27 | ins-->out | 1.6 |

Prosite Pattern Matches for 21615

>PS00001|PDOC00001|ASN_GLYCOSYLATION N-glycosylation site.

Query:   39      NESK      42

Query:   130     NMSS      133

>PS00005|PDOC00005|PKC_PHOSPHO_SITE Protein kinase C phosphorylation site.

Query:   60      TKK       62

Query:   137     SVK       139

Query:   149     TTK       151

Query:   208     TGR       210

>PS00006|PDOC00006|CK2_PHOSPHO_SITE Casein kinase II phosphorylation site.

Query:   89      TVLD      92

Query:   184     SLQE      187

Query:   213     TAEE      216

>PS00007|PDOC00007|TYR_PHOSPHO_SITE Tyrosine kinase phosphorylation site.

Query:   42      KLQELEKY      49

>PS00008|PDOC00008|MYRISTYL N-myristoylation site.

Query:   17      GIGQAA    22

Query:   126     GNIINM    131

Query:   156     GLTKSV    161

Query:   169     GIRCNC    174

>PS00061|PDOC00060|ADH_SHORT Short-chain alcohol dehydrogenase family signature.

Query:   147     YSTTKAAVIGL      157

FIGURE 22

21612, NOVEL HUMAN DEHYDROGENASES

FIELD OF THE INVENTION

The present invention relates to newly identified human alcohol dehydrogenases (ADHs) belonging to the superfamily of mammalian dehydrogenases/reductases. The invention also relates to polynucleotides encoding the alcohol dehydrogenases. The invention further relates to methods using the alcohol dehydrogenase polypeptides and polynucleotides as a target for diagnosis and treatment in ADH-mediated or -related disorders. The invention further relates to drug-screening methods using the alcohol dehydrogenase polypeptides and polynucleotides to identify agonists and antagonists for diagnosis and treatment. The invention further encompasses agonists and antagonists based on the alcohol dehydrogenase polypeptides and polynucleotides. The invention further relates to procedures for producing the alcohol dehydrogenase polypeptides and polynucleotides.

BACKGROUND OF THE INVENTION

Alcohol dehydrogenases are common enzymes in nature and are often characterized as members of either the MDR (medium-chain dehydrogenase/reductase) or SDR (short-chain dehydrogenase/reductase) protein families. Members of the SDR and MDR families appear to have similar activities though they work via different mechanisms and structures. The SDR superfamily comprises isomerases, lyases and oxidoreductases. The enzymes of this family cover a wide range of substrate specificities including steroids, alcohols, and aromatic compounds, however, most family members are known to be $NAD^+$- or $NADP^+$-dependent oxidoreductases. In the combined SDR superfamily, only a single tyrosine residue is strictly conserved and ascribed a critical enzymatic function. Members of the MDR superfamily are often multimeric enzymes associated with 0, 1, or 2 zinc atoms. Substrates of the MDR enzymes are often alcohols and aldehydes. Six different classes of mammalian ADH isoforms are members of the MDR family. In addition to the MDR and SDR families, alcohol dehydrogenases have also been associated with protein families reflecting iron-dependant enzymes, long-chain enzymes, and several types of prokaryotic enzymes with other cofactor requirements.

Most dehydrogenase proteins function as dimers or tetramers and possess at least two domains: the first domain comprising the coenzyme binding site, and the second domain comprising the substrate binding site. This latter domain determines the substrate specificity and contains the amino acids involved in catalysis. ADHs have a variety of substrate specificities, but act primarily on primary or secondary alcohols, hemiacetals, cyclic secondary alcohols, or on the corresponding aldehydes and ketones. The catalytic role of ADH in mammalian ethanol oxidation is well studied. ADH catalyzes the conversion of ethanol to acetaldehyde using $NAD^+$ as a cofactor. Specifically, the coenzyme binds ADH, followed by an interaction with ethanol, the ethanol is subsequently converted to acetaldehyde and the $NAD^+$ is converted to NADH. Members of the mammalian ADH protein family have varying electrophoretic mobilities, Michaelis constants (binding affinities) for ethanol, and sensitivities to pyrazol inhibition. For instance, class I ADHs have low $K_m$ values (less than 5 mM) for ethanol oxidation while class II and class IV ADHs have intermediate $K_m$ values (about 30 mM). Class III ADH enzymes are not saturable with ethanol and virtually function exclusively as glutathione-dependent formaldehyde dehydrogenases. Allelic variation of the mammalian genes have been identified. The kinetic properties of the resultant variants differ significantly owing to single amino acid substitutions in the coenzyme binding domains of the enzymes.

Alcohol dehydrogenases play fundamental roles in degradative, synthetic, and detoxification pathways and have been implicated in a variety of critical developmental processes and pathophysiological disease states. For instance, allelic variations of ADH2 and ADH3 appear to influence the susceptibility to alcoholism and alcoholic liver cirrhosis in Asians (Thomasson et al. (1991) *Am. J. Hum Genet.* 48:677–681, Chao et al. (1994) *Hepatology* 19:360–366, and Higuchi et al. (1995) *Am. J. Psychiatry* 152:1219–1221). Furthermore, first-pass metabolism is the difference between the quantity of ethanol that reaches the systemic circulation by the intravenous route and the quantity that entered by the oral dose. Several lines of evidence now indicate that first-pass metabolism of alcohol in humans may occur in the liver via the activity of members of the mammalian ADH family (Yin et al. (1999) *Enzymology and Molecular Biology of Carbonyl Metabolism* 7, Plenum Publishers, New York).

ADHs are also involved in detoxification pathways. For instance, class III ADH is unsaturable by ethanol and mainly functions as a glutathione-dependant formaldehyde dehydrogenase and is therefore important for the elimination of endogenously formed formaldehyde. ADHs are also involved in the metabolism of nitrobenzaldehyde, a dietary carcinogen. It has been suggested that the lack of σ-ADH in Japanese patients may lead to a decreased detoxification of the dietary carcinogen nitrobenzaldehyde and may possible be linked to the high rate of gastric cancer in Japanese (Baron et al. (1991) *Life Sci* 49:1929–34; Grab et al. (1977) *Cancer Res* 37:4181–90 and Seedcake et al. (1980) *Rev Ed* 9:346–51). ADH is also involved in the activation of 1,2 dimethylhydrazine, an experimentally used procarcinogen.

Retinoic acid is a ligand controlling a nuclear receptor signaling pathway that plays a key role in the regulation of embryonic development, spermatogenesis, and epithelial differentiation (Chambon et al. (1996) *FASEB J.* 10:940–954 and Mangelsdorf et al. (1995) *Cell* 83:841–850). The synthesis of retinoic acid occurs via the oxidation of retinol to retinal followed by the conversion of retinal to retinoic acid. Members of the alcohol dehydrogenase and short-chain dehydrogenase/reductase families catalyze the reversible, rate limiting conversion of retinol to retinal, while the oxidation of retinal to retinoic acid is catalyzed by members of the aldehyde dehydrogenase or P450 enzyme families (Deuster et al. (1996) *Biochemistry* 35:12221–12227). Therefore, members of the ADH family influence the growth and developmental processes mediated by the active metabolite retinoic acid.

ADH metabolism of retinol to retinal is inhibited by ethanol, and this may lead to altered epithelial cell differentiation and malignant cell transformation. Furthermore, it has been suggested that the ability of ethanol to inhibit the oxidation of retinol by ADH underlies the pathology of fetal alcohol syndrome, a birth defect characterized by craniofacial, limb, and brain malformations (Duester el al. (1991) *Alcohol Clin Exp Res* 15:568–572). Retinoic acid also functions to maintain differentiation of epithelial cells and influences spermatogenesis in adult vertebrates (Chambon et al. (1996) *FASEB J.* 10:940–954). Data suggests that retinoic acid signaling in spermatogenesis and keratinocyte differentiation may be significantly disrupted by ethanol through ADH pathways. It has been proposed that inhibition of retinol metabolism by ethanol may be responsible for the testicular atrophy and spermatogenesis commonly seen in male chronic alcoholics. Furthermore, skin diseases such as psoriasis, have been associated with heavy drinking.

ADH may also play a role in colorectal cancers. During colorectal carcinogenesis, ADH activity is significantly decreased in polyps and further decreased in cancer tissue. (Egerer et al. (1997) *Gastroenterology* 112:A1260). Furthermore, epidemiological studies have demonstrated that alcohol consumption is a risk factor for development of oral, esophageal, colorectal, and upper gastrointestinal cancers (Blot et al. (1992) *Cancer Res* 52:2119s–2123s). The role of ADH in cancers of these various tissues may result from the production of acetaldehyde following oxidation of ethanol by ADH, an alteration in retinol metabolism or through the role of ADH in carcinogen metabolism.

Further functional links between disease and the oxidative/reductive actions of various dehydrogenases are being established. For instance, ERAB is a member of the short-chain dehydrogenase/reductase family. Interactions between and Amyloid β peptide and ERAB have been shown to mediate neurotoxicity and apoptosis in neuronal cell lines (Yan et al. (1997) *Nature* 389:689–693) and thus are being implicated in the pathogenesis of neurodegenerative disorders like Alzheimer's disease (Oppermann et al. (1999) *Enzymology and Molecular Biology of Carbonyl Metabolism* 7, Plenum Publishers, New York and Oppermann et al. (1999) *FEBS Letters* 451:238–242).

Accordingly, ADHs are a major target for drug action and development. Therefore, it is valuable to the field of pharmaceutical development to identify and characterize previously unknown ADHs. The present invention advances the state of the art by providing previously unidentified human alcohol dehydrogenases.

SUMMARY OF THE INVENTION

It is an object of the invention to identify novel alcohol dehydrogenases.

It is a further object of the invention to provide novel alcohol dehydrogenase polypeptides that are useful as reagents or targets in assays applicable to treatment and diagnosis of ADH-mediated or -related disorders.

It is a further object of the invention to provide polynucleotides corresponding to the novel ADH polypeptides that are useful as targets and reagents in ADH assays applicable to treatment and diagnosis of ADH-mediated or -related disorders and useful for producing novel ADH polypeptides by recombinant methods.

A specific object of the invention is to identify compounds that act as agonists and antagonists and modulate the expression of the novel ADHs.

A further specific object of the invention is to provide compounds that modulate expression of the alcohol dehydrogenases for treatment and diagnosis of ADH-related disorders.

The invention is thus based on the identification of novel human alcohol dehydrogenases. The amino acid sequence for ADH 21620, 33756, 21676, 21612, and 21615, are shown in SEQ ID NOS:1, 3, 5, 7, and 9, respectfully. The nucleotide sequence for ADH 21620, 33756, 21676, 21612, and 21615 are shown in SEQ ID NOS:2, 4, 6, 8, and 10, respectfully.

The invention provides isolated ADH polypeptides, including a polypeptide having the amino acid sequence shown in SEQ ID NOS:1, 3, 5, 7, and 9, or the amino acid sequence encoded by the cDNA deposited as ATCC Patent Deposit No. PTA-2170 on Jun. 27, 2000 ("the deposited cDNA"); as ATCC Patent Deposit No. PTA-2812 on Dec. 15, 2000; as ATCC Patent Deposit No. PTA-2171 on Jun. 27, 2000; or as ATCC Patent Deposit No. PTA-2813 on Dec. 15, 2000; for 21612, 21615, 21620, and 21676, respectively.

The invention also provides isolated ADH nucleic acid molecules having the sequences shown in SEQ ID NOS:2, 4, 6, 8, and 10, or in the deposited cDNA.

The invention also provides variant polypeptides having an amino acid sequence that is substantially homologous to the amino acid sequences shown in SEQ ID NOS:1, 3, 5, 7, and 9, or encoded by the deposited cDNA.

The invention also provides variant nucleic acid sequences that are substantially homologous to the nucleotide sequences shown in SEQ ID NOS:2, 4, 6, 8, and 10, or in the deposited cDNA.

The invention also provides fragments of the polypeptides shown in SEQ ID NOS:1, 3, 5, 7, and 9, and nucleotide sequences shown in SEQ ID NOS:2, 4, 6, 8, and 10, as well as substantially homologous fragments of the polypeptides or nucleic acids.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the ADH nucleic acid molecules and polypeptides, and particularly recombinant vectors and host cells.

The invention also provides methods of making the vectors and host cells and methods for using them to produce the ADH nucleic acid molecules and polypeptides.

The invention also provides antibodies or antigen-binding fragments thereof that selectively bind the ADH polypeptides and fragments.

The invention also provides methods of screening for compounds that modulate expression or activity of the ADH polypeptides or nucleic acid (RNA or DNA).

The invention also provides a process for modulating ADH polypeptide or nucleic acid expression or activity, especially using the screened compounds. Modulation may be used to treat conditions related to aberrant activity or expression of the ADH polypeptides or nucleic acids.

The invention also provides assays for determining the activity of or the presence or absence of the ADH polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the nucleotide sequence (SEQ ID NO:2) and the deduced amino acid sequence (SEQ ID NO:1) of the novel 21620 ADH.

FIG. 4 shows an analysis of the 21620 ADH open reading frame for amino acids (SEQ ID NO:1) corresponding to specific functional sites. A putative protein kinase C phosphorylation site is found from about amino acid 135 to about amino acid 137. Putative casein kinase II phosphorylation sites are found from about amino acid 72 to about amino acid 75, from about amino acid 89 to about amino acid 92, and from about amino acid 135 to about amino acid 138. Putative N-myristoylation sites are found from about amino acid 18 to about amino acid 23, from about amino acid 24 to about amino acid 29, from about amino acid 40 to about amino acid 45, from about amino acid 90 to about amino acid 95, from about amino acid 109 to about amino acid 114, and from about amino acid 199 to about amino acid 204. In addition, amino acids corresponding to the short-chain alcohol dehydrogenase family signature are found in the sequence at about amino acids 166 to 176.

FIG. 7 shows the nucleotide sequence (SEQ ID NO:4) and the deduced amino acid sequence (SEQ ID NO:3) of the novel 33756 ADH.

FIG. 10 shows an analysis of the 33756 ADH open reading frame (SEQ ID NO:3) for amino acids corresponding to specific functional sites. A putative N-glycosylation site is found from about amino acid 100 to about amino acid 103. Putative protein kinase C phosphorylation sites are found from about amino acid 29 to about amino acid 31, from about amino acid 32 to about amino acid 34, from about amino acid 120 to about amino acid 122, from about amino acid 144 to about amino acid 146, from about amino acid 213 to about amino acid 215, from about amino acid 242 to about amino acid 244, and from about amino acid 252 to about amino acid 254. Putative casein kinase II phosphorylation sites are found from about amino acid 32 to about amino acid 35, from about amino 63 to about amino acid 66, and from about amino acid 252 to about amino acid 255. Putative N-myristoylation sites are found from about amino acid 149 to about amino acid 154, from about amino acid 160 to about amino acid 165, and from about amino acid 171 to about amino acid 176.

FIG. 11 shows the nucleotide sequence (SEQ ID NO:5) and the deduced amino acid sequence (SEQ ID NO:6) of the novel 21676 ADH.

FIG. 14 shows an analysis of the 21676 ADH open reading frame (SEQ ID NO: 5) for amino acids corresponding to specific functional sites. A putative N-glycosylation site is found from about amino acid 171 to about amino acid 174. A putative protein kinase C phosphorylation sites are found from about amino acid 100 to about amino acid 102, from about amino acid 103 to about amino acid 105, from about amino acid 191 to about amino acid 193, from about amino acid 215 to about amino acid 217, from about amino acid 284 to about amino acid 286, from about amino acid 313 to about amino acid 315, and from about amino acid 323 to about amino acid 325. A putative casein kinase II phosphorylation sites are found from about amino acid 54 to about amino acid 57, from about amino 103 to about amino acid 106, from about amino acid 134 to about amino acid 137, and from about amino acid 323 to about amino acid 326. Putative N-myristoylation sites are found from about amino acid 12 to about amino acid 17, from about amino acid 28 to about amino acid 33, from about amino acid 45 to about amino acid 50, from about amino acid 220 to about amino acid 225, from about amino acid 231 to about amino acid 236, and from about amino acid 242 to about amino acid 247.

FIG. 15 shows the nucleotide sequence (SEQ ID NO:7) and the deduced amino acid sequence (SEQ ID NO:8) of the novel 21612 ADH.

FIG. 18 shows an analysis of the 21612 ADH open reading frame (SEQ ID NO:7) for amino acids corresponding to specific functional sites. A putative N-glycosylation site is found from about amino acid 101 to about amino acid 104. A putative protein kinase C phosphorylation sites are found from about amino acid 5 to about amino acid 7, from about amino acid 115 to about amino acid 117, from about amino acid 282 to about amino acid 284, from about amino acid 313 to about amino acid 315, from about amino acid 381 to about amino acid 383, and from about amino acid 392 to about amino acid 394. A putative casein kinase II phosphorylation sites are found from about amino acid 56 to about amino acid 59, from about amino acid 320 to about amino acid 323, from about amino acid 338 to about amino acid 341, and from about amino acid 372 to about amino acid 375. A putative N-myristoylation sites are found from about amino acid 17 to about amino acid 22, from about amino acid 52 to about amino acid 57, from about amino acid 128 to about amino acid 133, and from about amino acid 353 to about amino acid 358. In addition, a microbodies C-terminal targeting signal is found from about amino acid 416 to about amino acid 418.

FIG. 19 shows the nucleotide sequence (SEQ ID NO:10) and the deduced amino acid sequence (SEQ ID NO:9) of the novel 21615 ADH.

FIG. 22 shows an analysis of the 21615 ADH open reading frame (SEQ ID NO:9) for amino acids corresponding to specific functional sites. Putative N-glycosylation sites are found from about amino acid 39 to about amino acid 42 and from about amino acid 130 to about 133. Putative protein kinase C phosphorylation site are found from about amino acid 60 to about amino acid 62, from about amino acid 137 to about amino acid 139, from about amino acid 149 to about amino acid 151, and from about amino acid 208 to about amino acid 210. Putative casein kinase II phosphorylation sites are found from about amino acid 89 to about amino acid 92, from about amino acid 184 to about amino acid 187, from about amino acid 213 to about amino acid 216. A putative tyrosine kinase site is found from about amino acid 42 to about amino acid 49. Putative N-myristoylation sites are found from about amino acid 17 to about amino acid 22, from about amino acid 126 to about amino acid 131, from about amino acid 156 to about amino acid 161, and from about amino acid 169 to about amino acid 174. In addition, a short-chain alcohol dehydrogenase family signature is found from about amino acid 147 to about amino acid 157.

DETAILED DESCRIPTION OF THE INVENTION

Polypeptides

The invention is based on the discovery of novel human alcohol dehydrogenases. Specifically, an expressed sequence tag (EST) was selected based on homology to the alcohol dehydrogenase sequence. This EST was used to design primers based on sequences that it contains and used to identify cDNAS from human cDNA libraries, including primary osteoblasts. Positive clones were sequenced and the overlapping fragments were assembled. Analysis of each of the assembled sequences revealed that the cloned cDNA molecules encode ADHs.

The invention thus relates to novel ADHs having the deduced amino acid sequence shown in FIGS. 1, 7, 11, 15, and 19, or the amino acid sequences shown in SEQ ID NOS:1, 3, 5, 7, and 9, or the amino acid sequences encoded by the cDNA inserts of the plasmids deposited as ATCC Patent Deposit Nos. PTA-2170, PTA-2812, PTA-2171, and PTA-2813.

The deposits will be maintained under the terms of the Budapest Treaty on the International Recognition of the Deposit of Microorganisms. The deposits are provided as a convenience to those of skill in the art and is not an admission that a deposit is required under 35 U.S.C. § 112. The deposited sequences, as well as the polypeptides encoded by the sequences, are incorporated herein by reference and controls in the event of any conflict, such as a sequencing error, with description in this application.

"ADH polypeptide" or "ADH protein" refers to the polypeptides in SEQ ID NOS:1, 3, 5, 7, and 9, or the polylpeptides encoded by the deposited cDNAs. The term "ADH protein" or "ADH polypeptide", however, further includes the numerous variants described herein, as well as fragments derived from the full-length ADHs and variants.

Figure 2:
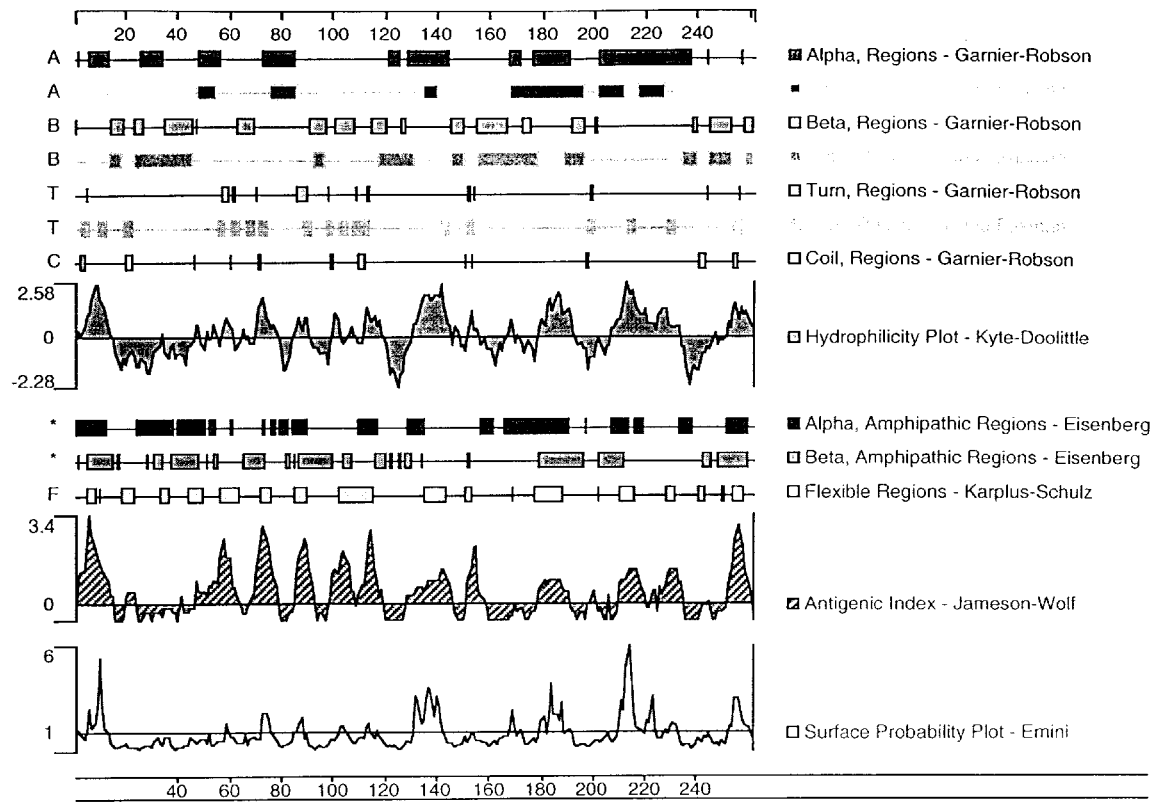
FIG. 2 shows an analysis of the 21620 ADH amino acid sequence: αβturn and coil regions; hydrophilicity; amphipathic regions; flexible regions; antigenic index; and surface probability plot.
Figure 3:
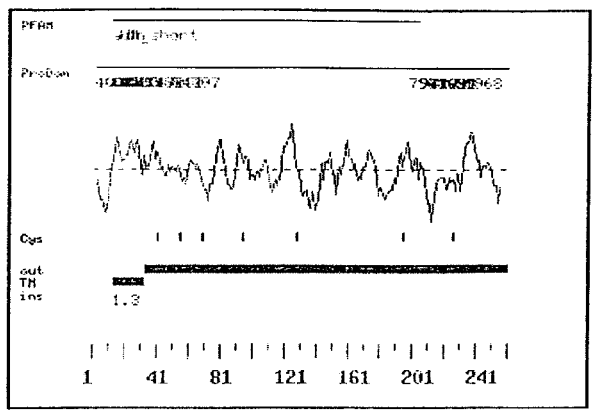
FIG. 3 shows a hydrophobicity plot of the 21620 ADH amino acid sequence (SEQ ID NO:1). Also shown is the predicted transmembrane segment from about amino acid 13 to about amino acid 32. In addition, a graphical representation of the functional domain of ADH short chain is also shown.
Figure 5:
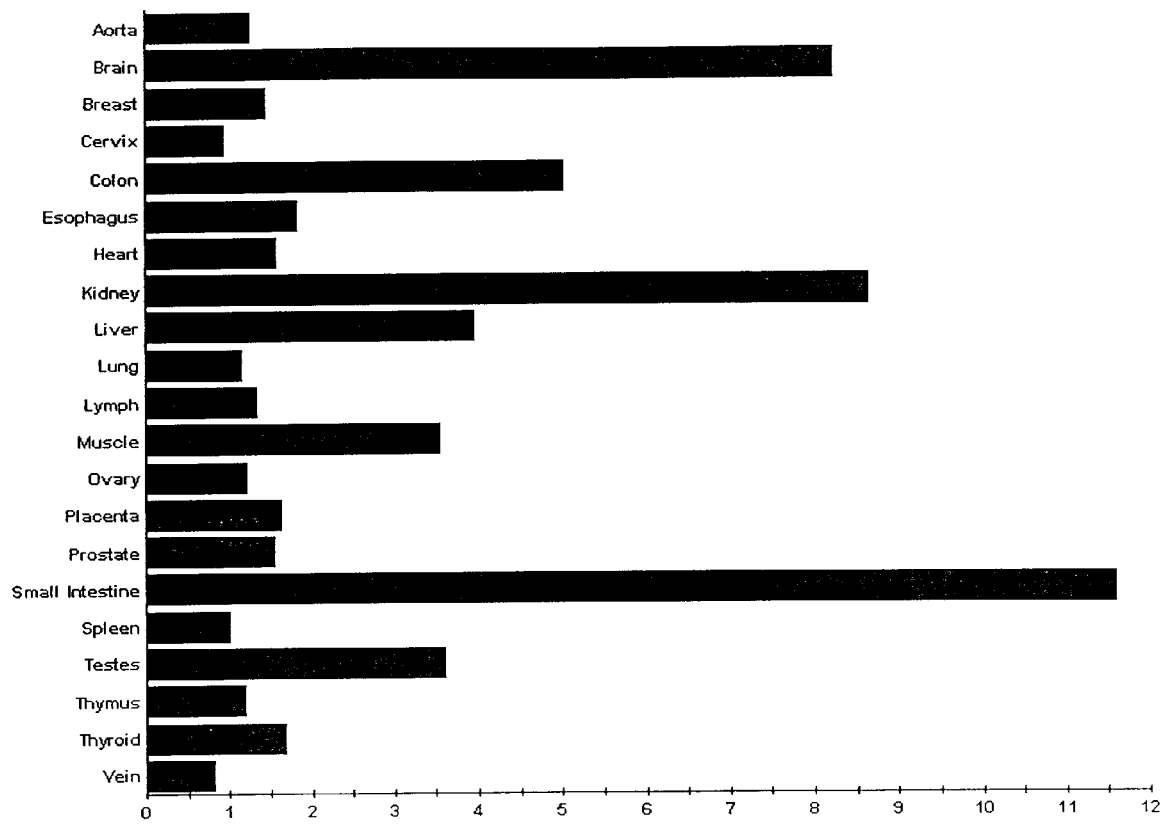
FIG. 5 shows expression of the 21620 ADH mRNA in various tissues. The expression data was derived from a reverse Northern using Taqman.
Figure 6:
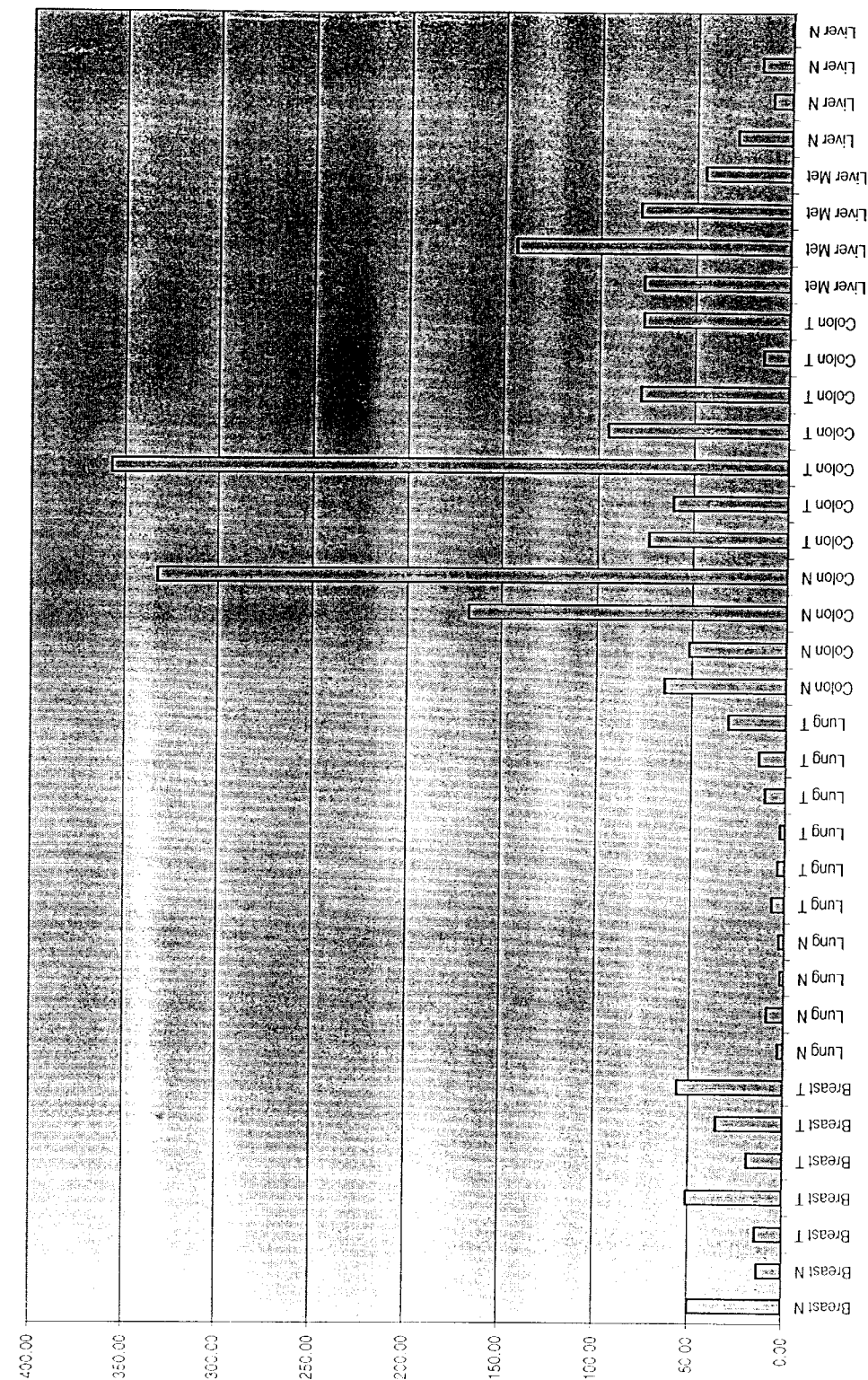
FIG. 6 shows expression of the 21620 ADH mRNA in normal and malignant breast, lung, liver and colon tissues. The liver metastases are derived from malignant colonic tissue. The expression data was derived from a reverse Northern using Taqman.
Figure 8:
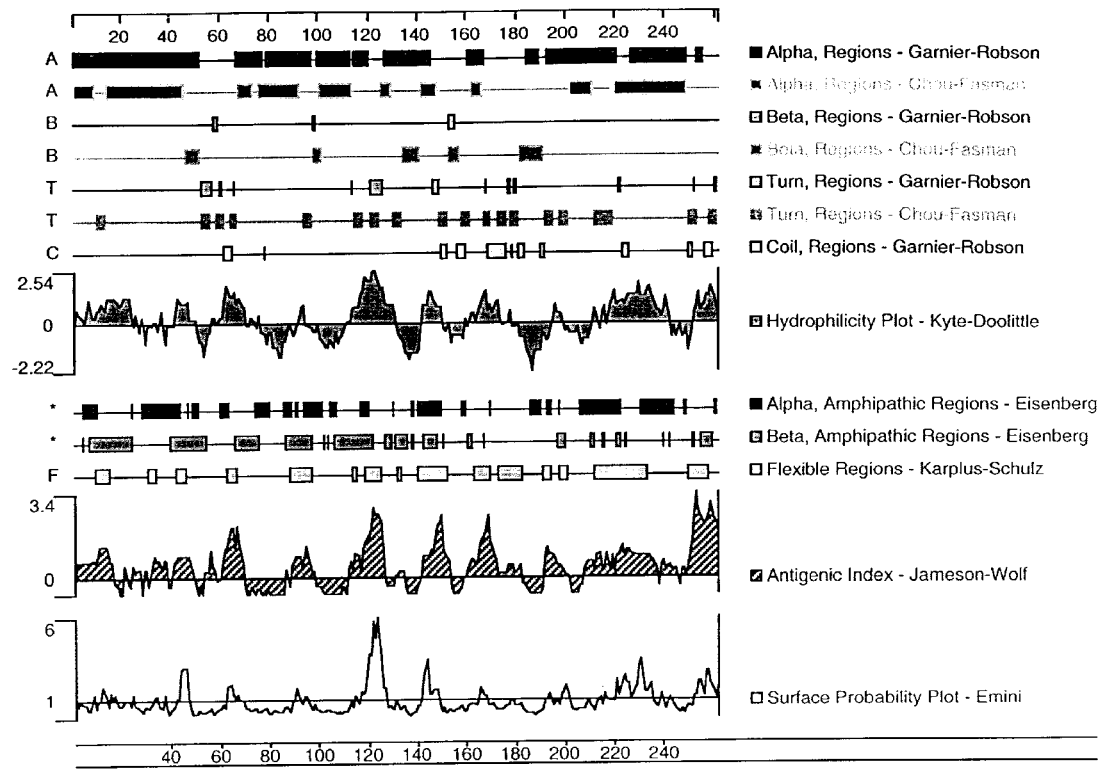
FIG. 8 shows an analysis of the 33756 ADH amino acid sequence: αβturn and coil regions; hydrophilicity; amphipathic regions; flexible regions; antigenic index; and surface probability plot.
Figure 9:
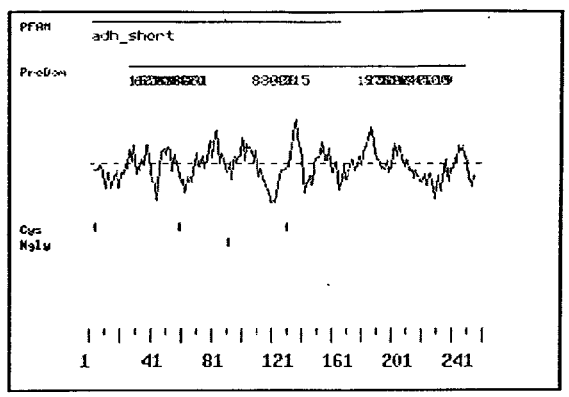
FIG. 9 shows a hydrophobicity plot of the 33756 ADH amino acid sequence (SEQ ID NO:3). Also shown is a graphical representation of the functional domain of ADH short chain.
Figure 12:
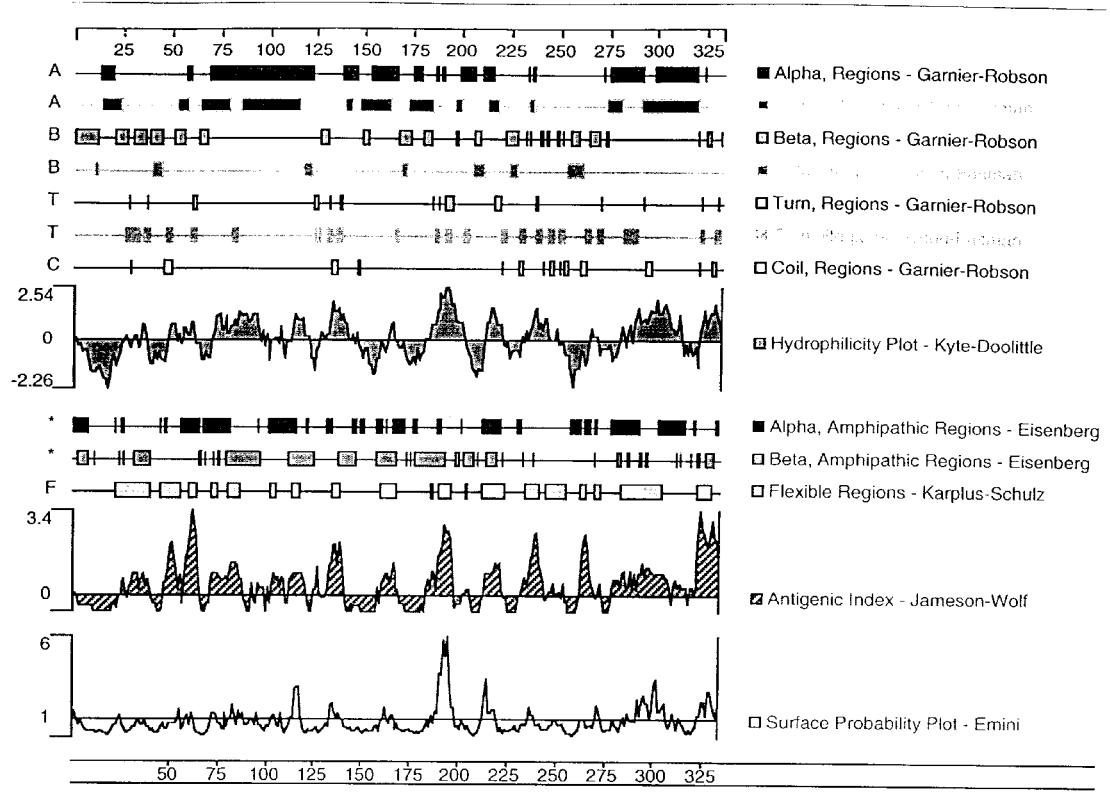
FIG. 12 shows an analysis of the 21676 ADH amino acid sequence: αβturn and coil regions; hydrophilicity; amphipathic regions; flexible regions; antigenic index; and surface probability plot.
Figure 13:
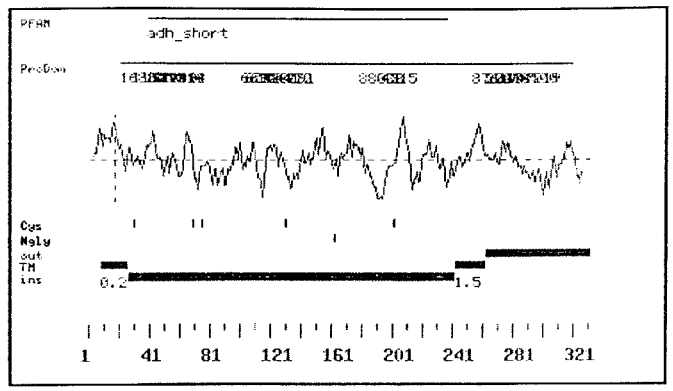
FIG. 13 shows a hydrophobicity plot of the 21676 ADH amino acid sequence (SEQ ID NO:5). Also shown is the predicted amino terminus signal peptide sequence. In addition, two transmembrane segments are predicted for the full-length polypeptide from about amino acid 8 to about amino acid 25 and from about amino acid 242 to about amino acid 261. In the mature form of the polypeptide the transmembrane domain is predicted from about amino acid 226 to about amino acid 245. Also shown is a graphical representation of the functional domain of ADH short chain.
Figure 16:
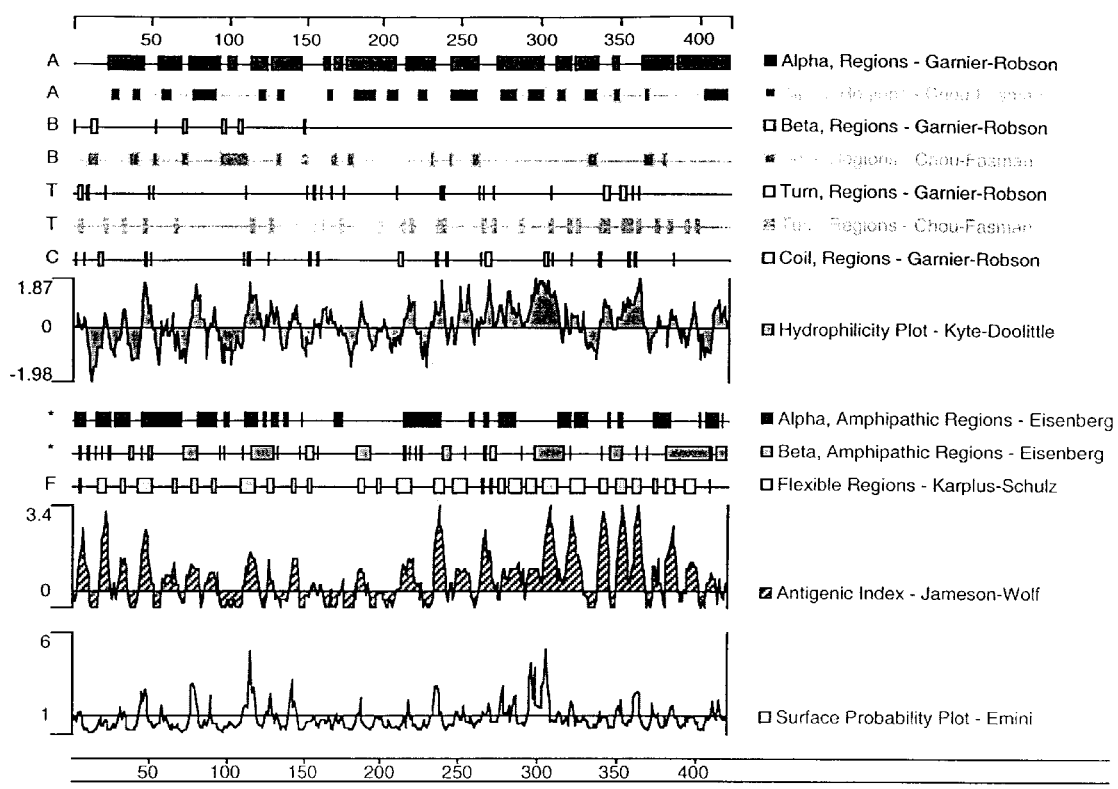
FIG. 16 shows an analysis of the 21612 ADH amino acid sequence: αβturn and coil regions; hydrophilicity; amphipathic regions; flexible regions; antigenic index; and surface probability plot.
Figure 17:
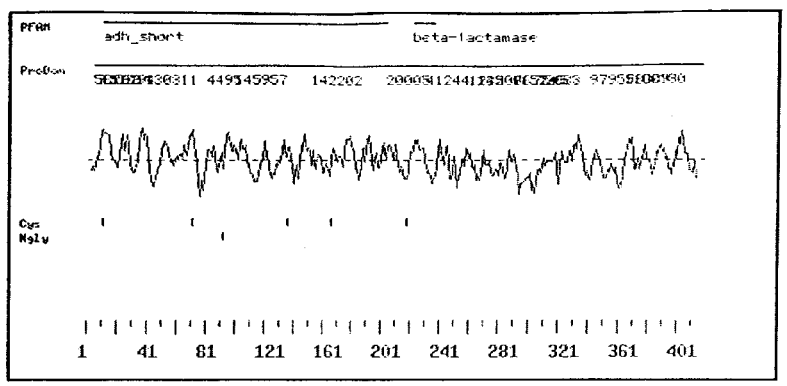
FIG. 17 shows a hydrophobicity plot of the 21612 ADH amino acid sequence (SEQ ID NO:7). Also shown is a graphical representation of the functional domain of ADH short chain.
Figure 20:
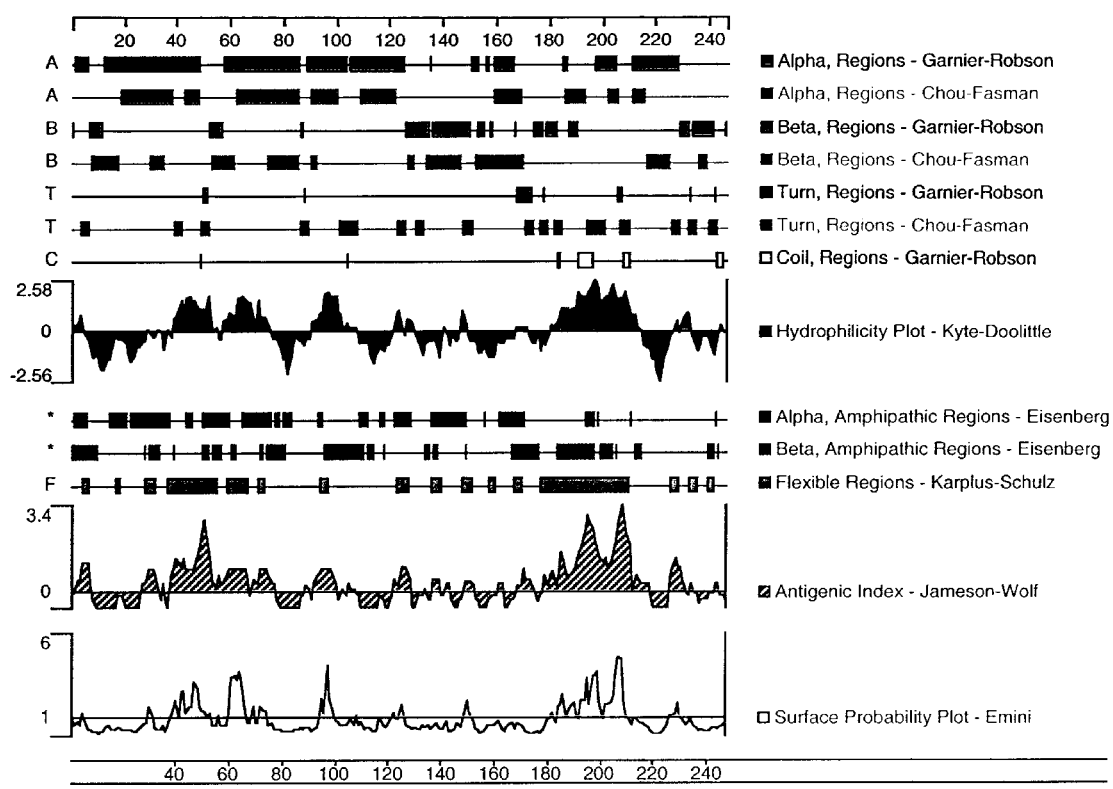
FIG. 20 shows an analysis of the 21615 ADH amino acid sequence: αβturn and coil regions; hydrophilicity; amphipathic regions; flexible regions; antigenic index; and surface probability plot.
Figure 21:
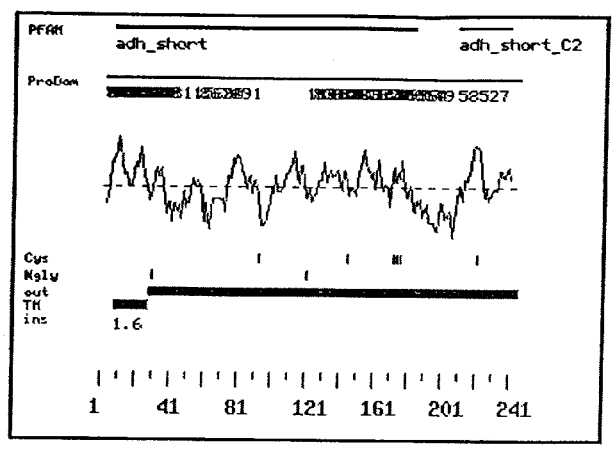
FIG. 21 shows a hydrophobicity plot of the 21615 ADH amino acid sequence (SEQ ID NO:9). Also shown is the predicted transmembrane segment from about amino acid 8 to about amino acid 27. In addition, a graphical representation of the functional domain of ADH short chain is also shown.

Tissues and/or cells in which the 21620 ADH is found include, but are not limited to those shown in FIGS. 5 and 6. Tissues in which the gene is highly expressed include brain, colon, kidney, and small intestine. Moderate expression occurs in liver, muscle, and testes. Lower positive expression occurs in the aorta, breast, cervix, esophagus, heart, lung, lymph, ovary, placenta, spleen, thymus, thyroid, and vein. The 21620 ADH is also expressed in malignant breast, lung, and colon tissue, and in liver metastases derived from malignant colonic tissue.

The present invention thus provides isolated or purified polypeptides of the 21620 ADH, 33756 ADH, 21676 ADH, 21612 ADH, and 21615 ADH and variants and fragments thereof.

The short-chain alcohol dehydrogenase family signature is found in the 21620 ADH from about amino acid 166 to about amino acid 176 and in the 21615 ADH from about amino acid 147 to about amino acid 157.

Based on a Blast search, highest homology to the 21620 ADH was shown to Antennal-specific Short-chain Dehydrogenase/reductase from *Drosophila melanogaster* (Genbank Acc. No. AF 116553) and to the Oxidoreductase from *Haloferax volcani* (Genbank Acc. No. U95375).

Based on a Blast search, highest homology to the 33756 ADH was shown to CGI-82 from *Homo sapiens* (Genbank Acc. No. AF 151840), UBE-1 b from *Mus musculus* (Genbank Acc. No. AB030504), UBE-1a from *Mus musculus* (Genbank Acc. No. AB030503).

Based on a Blast search, no significant homology was found to the 21676 ADH.

Based on a Blast search, highest homology to the 21612 ADH was shown to a protein similar to alcohol dehydrogenase from *C. elegans* (Genbank Acc. No. U28739), a protein similar to alcohol dehydrogenase from *C. elegans* (Genbank Acc. No. Z74029), and to the hypothetical protein RV3224 from *Mycobacterium tuberculosis* (Genbank Acc. No. Z95120).

Based on a Blast search, highest homology to the 21615 ADH was shown to a 3-oxoacyl-(acyl carrier protein) reductase from *Thermotoga maritima* (Genbank Acc. No. AAD36790).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The ADH polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the ADH having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An ADH polypeptide is also considered to be isolated when it is part of a membrane preparation or is purified and then reconstituted with membrane vesicles or liposomes.

The language "substantially free of chemical precursors or other chemicals" includes preparations of the ADH polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the ADH polypeptides comprise the amino acid sequences shown in SEQ ID NOS:1, 3, 5, 7, and 9. However, the invention also encompasses sequence variants. Variants include a substantially homologous protein encoded by the same genetic locus in an organism, i.e., an allelic variant.

The 21620 ADH has been mapped to human chromosome 17 (17q12–21) with flanking markers WI-3010 (9.7cR) and WI-4251 (17.3cR). Mutations near this locus include, but are not limited to, the following: wilms tumor 4; patella aplasia or hypoplasia; psoriasis susceptibility 2 (psors2); malignant hyperthermia susceptibility 2 (MSH2); pallidopontonigral degeneration (PPND); pseudohypoaldosteronism type II locus B; and gliosis and familial progressive subcortical. In the mouse this locus is associated with the following: susceptibility to lung cancer (Sluc4); pulmonary adenoma resistance (Par1); radiation-induced apoptosis 4 (Rapop4); cocked (co); open eyelids (oe); ovum mutant (Om); rimy (rmy); susceptibility to experimental allergic encephalomyelitis 7 (Eae7); liver weight QTL 4 (Lwq4); alopecia (A1); spleen weight OTL 1 (Swq1); modifier of von willebrand factor (Mvwf); neuron number control (Nnc1); recombination induced mutation 3 (rim3); bald-arthritic (Bda); bare skin (Bsk); rex (re); alymphoplasia (aly); cleft lip 1 (clf1); seizure susceptibility 3 (Szs3); uncovered (Uncv). Genes near this locus include CDC18L, RARA, PDE6G, IGFBP4, TCFL4, NAGLU, FZD2, PYY, ERBB2, RABL, SCYA11, KRT12, NEUROD2, SLC6A4, ACACA, SCYA1, and BRCA1.

The 21612 ADH has been mapped to human chromosome 9 (9q22–33) with flanking markers WI-6207 (5.7 cR) and D9S174 (6.0 cR). Mutations near this locus include, but are not limited to, the following: hypomagnesemia with secondary hypocalcemia (HOMG); hemophagocytic lymphohistiocytosis, familial 1; nephronophthisis (NPHP2), infantile; HSN1, neuropathy, hereditary sensory, type 1; high density lipoprotein deficiency (HDLDT1), tangier type 1; dysautonomia (dys), familial; muscular dystrophy, limb-girdle, type 2H; acrofacial dysostosis 1 (AFD1), nager type; amyotrophic lateral sclerosis 4 (ALS4), juvenile; and multiple self-healing squamous epithelioma (MSSE). In the mouse this locus is associated with the following: vacillans (vc), whirler (wi), ochre (och), Hertwig's anemia (an), b-associated fitness (baf), iris stromal atrophy (isa), lymphoma resistance (lyr), and systemic lupus erythmatosus susceptibility 2 (sle2). Genes near this locus include SCYA5, ZFP37, UGCG, SLC31A2, HXB, HPRP4P, ORM1, TNFSF8, TXN, IKBAKAP, PTPN3, EDG2, CSMF, chondrosarcoma, myxoid extraskeletal, and fused to EWS.

Variants also encompass proteins derived from other genetic loci in an organism, but having substantial homology to the ADHs of SEQ ID NOS:1, 3, 5, 7, and 9. Variants also include proteins substantially homologous to the ADHs but derived from another organism, i.e., an ortholog. Variants also include proteins that are substantially homologous to the ADHs that are produced by chemical synthesis. Variants also include proteins that are substantially homologous to the ADHs that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NOS:2, 4, 6, 8, and 10 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the ADH. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. For example, variants of the ADHs can have an altered developmental expression, temporal expression or tissue-preferred expression. ADH variants can also have an altered interaction with cellular components, substrates, coenzymes, metal ions, or ADH subunits. An altered interaction comprising either a higher or lower affinity of the ADH for the various cellular components, substrates, coenzymes, metal ions, or ADH subunits. By "coenzyme" is intended a molecule that is associated with the ADH and is essential for ADH activity. Some coenzymes are covalently linked to their enzyme while others are less tightly bound. A covalently linked coenzyme is referred to as a prosthetic group of the enzyme. By "coenzyme" is also intended the oxidized or reduced product of the coenzyme which is formed following the enzymatic reaction mediated by the ADH polypeptide. For example, in the biological oxidation of an alcohol to an aldehyde, a hydrogen ion is transferred to the coenzyme $NAD^+$ to form the coenzyme product NADH. Coenzymes of ADH include, but are not limited to, $NAD^+$ and $NAD^+$ analogues (Plapp et al. (1986) *Biochemistry* 25:5396–5402 and Yamazaki et al. (1984)*J. Biochem* 95:109–115), $\beta$-$NAD^+$(Favilla et al. (1980) Eur. J. Biochem 104, 223–227 and Creagh et al. (1993) *Biotechnol. Bioeng.* 41:156–161, benzoylpyridine adenine dinucleotide (Samama et al. (1986) *Eur. J. biochem.* 159:375–380), NADH, $NADP^+$, and NADPH. Variants of ADH may also have altered interactions with metal ions including, but not limited to, $Zn^{2+}$, $Co^{2+}$, $Mg^{2+}$, $Fe^{2+}$. See, for example, Yabe et al. (1992) *Biosci. Biotechnol. Biochem.* 56:338–339 and Leblov et al. (1972) *Phytochemistry* 11:1345–1346. Variants of ADH can also have an altered interaction with a substrate. Substrates of ADH include, but are not limited to, primary or secondary alcohols or hemiacetals, and cyclic secondary alcohols. By "substrate" is also intended the products resulting from the oxidation of the above mentioned substrates. Such products include, for example, various aldehydes and ketones. Other substrates include retinol, steroids, and carcinogens such as nitrobenzaldehyde and 1,2-dimethylhydrazine. Variants of ADH can also have an altered subunit interaction that affects the ability of ADH to form an active multimeric structure.

Useful variants of ADH polypeptides further include alterations in catalytic activity. The enzymatic reaction mediated by ADH is reversible and comprises either the oxidation, i.e., removal of electrons, of the above mentioned substrates or their reduction, i.e., addition of electrons. The catalytic reaction further comprises the oxidation or reduction of the coenzyme. Therefore, one embodiment involves a variant that results in binding of the substrate but results in slower oxidation/reduction or no oxidation/reduction of the substrate. Another variation can result in an increased rate of substrate oxidation/reduction. Other useful variation can include an altered binding affinity for a coenzyme or substrate. For example, an increased or decreased binding affinity of a coenzyme can alter the binding affinity of the ADH to the substrate and also alter the rate of substrate oxidation/reduction. Another variation can prevent the ADH monomer from associating with other ADH subunits to form an active multimeric complex.

Another useful variation provides a fusion protein in which one or more domains or subregions are operationally fused to one or more domains or subregions from another ADH. Specifically, a domain or subregion can be introduced that alters the coenzyme or substrate specificities or the rate of the enzymatic reaction.

Fully functional variants typically contain only conservative variations or variations in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the ADH polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as the binding affinity for the coenzyme or substrate or determining the catalytic constants for substrate oxidation/reduction. Sites that are critical for coenzyme and substrate binding can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

The assays for ADH enzyme activity are well known in the art and can be found for example, in Oppermann et al. (1999) FEBS 451:238–242, Thomasson et al. (1993) *Behavior Genetics* 23:131–136, and Zubey (1988) Macmillan Publishing Company, New York. These assays include, but are not limited to, determination of the Michaelis constants ($K_m$) or the dissociation constant for the ADH/substrate complex. Such analysis of enzyme activity may be performed spectrophotometrically by recording the change in absorbance of NAD$^+$. The catalytic efficiency or $k_{cat}$ can also be measured. $K_{cat}$ is defined as the maximum number of molecules of substrate converted to product per active site per unit of time. The specificity constant ($k_{cat}/K_m$) can also be used to measure the ability of the ADH to discriminate between competing substrates. Similar assays can also be performed to measure ADH/coenzyme interactions. In vivo measurements of ADH activity can be determined by pharmacokinetic studies. In such studies, an ethanol dose in administered and the blood ethanol concentration is monitored over time. The area under the time curve indicates the rate of ethanol elimination from the system. A larger blood alcohol concentration time curve indicates slower ethanol metabolism.

Substantial homology can be to the entire nucleic acid or amino acid sequence or to fragments of these sequences.

The invention thus also includes polypeptide fragments of the ADHs. Fragments can be derived from the amino acid sequences shown in SEQ ID NOS:1, 3, 5, 7, and 9. However, the invention also encompasses fragments of the variants of the ADHs as described herein.

The fragments to which the invention pertains, however, are not to be construed as encompassing fragments that may be disclosed prior to the present invention. Accordingly, a fragment of the 21620 ADH can comprise at least about 9, 15, 20, 25, 30, 35, 40 or more contiguous amino acids. A fragment of the 33756 ADH can comprise at least about 21, 25, 30, 35, 40, 45, 50, or more contiguous amino acids. A fragment of the 21676 ADH can comprise at least about 7, 10, 15, 20, 25, 30, 35 or more contiguous amino acids. A fragment of the 21612 ADH can comprise at least about 14, 20, 25, 30, 35, 40 or more contiguous amino acids. A fragment of the 21615 ADH can comprise at least about 7, 10, 15, 20, 25, 30, 35 or more contiguous amino acids. Fragments can retain one or more of the biological activities of the protein, for example the ability to bind a coenzyme or substrate or the ability catalyze the oxidation/reduction of a substrate. Alternatively, fragments can be used as an immunogen to generate ADH antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, substrate binding site, coenzyme binding site, short-chain alcohol dehydrogenase signature, microbodies C-terminal targeting signals, and sites for glycosylation, protein kinase C phosphorylation, casein kinase II phosphorylation, tyrosine kinase phosphorylation, and N-myristoylation. Further possible fragments include sites important for cellular and subcellular targeting.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the ADH or ADH variants. These epitope-bearing peptides are useful to raise antibodies that bind specifically to an ADH polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular site. Regions having a high antigenicity index are shown in FIGS. 2, 8, 12, 16, and 20, for the 21620, 33756, 21676, 21612, and 21615 ADHs, respectfully. However, intracellularly-made antibodies ("intrabodies") are also encompassed, which would recognize intracellular peptide regions.

The epitope-bearing ADH polypeptides may be produced by any conventional means (Houghten, R. A. (1985) *Proc. Natl. Acad Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the ADH fragment and an additional region fused to the carboxyl terminus of the fragment.

The invention thus provides chimeric or fusion proteins. These comprise an ADH peptide sequence operatively linked to a heterologous peptide having an amino acid sequence not substantially homologous to the ADH. "Operatively linked" indicates that the ADH peptide and the heterologous peptide are fused in-frame. The heterologous peptide can be fused to the N-terminus or C-terminus of the ADH or can be internally located.

In one embodiment the fusion protein does not affect ADH function per se. For example, the fusion protein can be a GST-fusion protein in which the ADH sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant ADH. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing an ADH polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An ADH-encoding nucleic acid can be cloned into such an expression vector such that the fusion moiety is linked in-frame to the ADH.

Another form of fusion protein is one that directly affects ADH functions. Accordingly, an ADH polypeptide is encompassed by the present invention in which one or more of the ADH domains (or parts thereof) has been replaced by homologous domains (or parts thereof) from another ADH or a short-chain dehydrogenase/reductase family member. Accordingly, various permutations are possible. For example, the substrate binding domain, or subregion thereof, can be replaced with the substrate binding domain or subregion from another ADH or a short-chain dehydrogenase/reductase family member. As a further example, the catalytic domain, or coenzyme binding domains or parts thereof, can be replaced with the appropriate domain from another ADH or SDR family member. Thus, chimeric ADHs can be formed in which one or more of the native domains or subregions has been replaced by another.

Additionally, chimeric ADH proteins can be produced in which one or more functional sites is derived from a different ADH or a short-chain dehydrogenase/reductase family member. It is understood however that sites could be derived from the ADH or a short-chain dehydrogenase/reductase family members that occur in the mammalian genome but which have not yet been discovered or characterized. Such sites include but are not limited to the catalytic site, substrate binding site, coenzyme binding site, sites important for targeting to subcellular and cellular locations, sites functional for interaction with ADH subunits, protein kinase A phosphorylation sites, glycosylation sites, and other functional sites disclosed herein.

The isolated ADHs can be purified from cells that naturally express it. Tissues and cells that express high levels of the 21620 ADH include, but are not limited to, brain, colon, kidney, and small intestine. Moderate levels of expression occur in the liver, muscle, and testes. Lower positive expression occurs in the aorta, breast, cervix, esophagus, heart, lung, lymph, ovary, placenta, spleen, thymus, thyroid, and vein. The 21620 ADH is also expressed in malignant breast, lung, and colon tissue, and liver metastases derived from colon. The ADHs of the present invention can also be purified from cells that have been altered to express it (recombinant), or synthesized using known protein synthesis methods.

In one embodiment, the protein is produced by recombinant DNA techniques. For example, a nucleic acid molecule encoding the ADH polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The ADH polypeptides are useful for producing antibodies specific for the ADH, regions, or fragments. Regions having a high antigenicity index score are shown in FIGS. 2, 8, 12, 16, and 20 for the 21620 ADH, 33756 ADH, 21676 ADH, 21612 ADH, and 21615 ADH, respectfully.

The ADH polypeptides are useful for biological assays related to ADHs. Such assays involve any of the known ADH functions or activities or properties useful for diagnosis and treatment of ADH-related conditions.

The ADH polypeptides are also useful in drug screening assays, in cell-based or cell-free systems. Cell-based systems can be native, i.e., cells that normally express the ADH, as a biopsy or expanded in cell culture. In one embodiment, however, cell-based assays involve recombinant host cells expressing the ADH.

Determining the ability of the test compound to interact with the ADH can also comprise determining the ability of the test compound to preferentially bind to the polypeptide as compared to the ability of a known binding molecule (e.g. a coenzyme or substrate) to bind to the polypeptide.

The polypeptides can be used to identify compounds that modulate ADH activity. Such compounds, for example, can increase or decrease the affinity of the substrate or coenzyme for ADH. Such compound can also increase or decrease the enzymatic activity of the ADH. Additionally, such compounds can also alter the interaction of ADH with a metal ion or alter the abliltiy of the ADH polypeptide to form a multimeric structure. Compounds that modulate ADH activity include, but are not limited to, pyrazole, 4-methylpyrazole, P-hydroxymercuribenzoate, o-Phenanthroline, iodoacetamide, iodoacetate, imidazole, colloidal bismuth subcitrate, cimetidine, ranitidine, and aspirin.

The ADHs of the present invention and appropriate variants and fragments can be used in high-throughput screens to assay candidate compounds for the ability to bind to the ADH. These compounds can be further screened against a functional ADH to determine the effect of the compound on the ADH activity. Compounds can be identified that activate (agonist) or inactivate (antagonist) the ADH to a desired degree. Modulatory methods can be performed in vitro (e.g., by culturing the cell with the agent) or, alternatively, in vivo (e.g., by administering the agent to a subject).

The ADH polypeptides can be used to screen a compound for the ability to stimulate or inhibit interaction between the ADH protein and a target molecule that normally interacts with the ADH protein. The target can be a coenzyme, metal ion, ADH substrate or another ADH subunit of the multimeric ADH enzyme. The assay includes the steps of combining the ADH protein with a candidate compound under conditions that allow the ADH protein or fragment to interact with the target molecule, and to detect the formation of a complex between the ADH protein and the target or to detect the biochemical consequence of the interaction with the ADH and the target, such as the oxidation/reduction of the substrate or coenzyme.

Determining the ability of the ADH to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length ADH or fragment that competes for substrate binding or cofactor binding, interferes with the ADH catalyzed reaction, or interferes with ADH subunit interactions. Other candidate compounds include mutant ADHs or appropriate fragments containing mutations that affect ADH function and thus compete for cofactor binding or substrate binding or interfere with the ADH catalyzed reaction or interfers with the ADH subunit interactions. Accordingly, a fragment that competes for substrate or coenzyme binding, for example with a higher affinity, or a fragment that binds substrate but does not catalyze its oxidation/reduction is encompassed by the invention.

The invention provides other end points to identify compounds that modulate (stimulate or inhibit) ADH activity. The assays typically involve an assay of events that result from substrate or coenzyme oxidation/reduction that indicate ADH activity. Thus, the expression of genes that are up- or down-regulated in response to the ADH enzyme can be assayed. In one embodiment, the regulatory region of such genes can be operably linked to a marker that is easily detectable, such as luciferase.

Any of the biological or biochemical functions mediated by the ADH can be used as an endpoint assay. These include all of the biochemical or biological events described herein, in the references cited herein and incorporated by reference, and other ADH functions known to those of ordinary skill in the art.

In the case of ADH, specific end points can include an altered NADH/NAD$^+$ ratio. For instance, ethanol oxidation results in an increased NADH/NAD$^+$ redox potential within the cytosol and mitochondria with subsequent alteration in several tissue metabolites. For example, the increase in cytosolic NADH/NAD$^+$ ratio causes an increase in the lactate/pyruvate ratio mediated via lactate dehydrogenase. Other consequences of ethanol- and acetaldehyde-induced redox changes include, enhanced triglyceride synthesis, inhibition of Krebs cycle activity, lactic acidosis, ketoacidosis, hyperuricaemia and enhanced fibrogenesis. See, for example, Peters et al. (1998) *Novartis Foundation Symposium* 216: 19–34, herein incorporated by reference.

Furthermore, the metabolism of ethanol via ADH results in the production of acetaldehyde, which is removed by the action of acetaldehyde dehydrogenases. Acetaldehyde alters various cellular function including glutathione depletion and inhibition of nuclear repair enzymes. Acetaldehyde can also alter cellular membranes resulting in severe cellular injury (Lieber et al. (1994) *Gastroenterology* 106:1085–105). Acetaldehyde toxicity depends on its net formation and can be increased when ADH activity is low and acetaldehyde dehydrogenase activity is high. Additional end points that can be assayed include biological events that are a consequence of ADH oxidation of retinol to retinal, which include but are not limited to differentiation of epithelium and spermatogenesis.

Binding and/or activating compounds can also be screened by using chimeric ADH proteins in which one or more domains, sites, and the like, as disclosed herein, or parts thereof, can be replaced by their heterologous counterparts derived from other ADHs or of any other short chain dehydrogenase/reductase family member. For example, a substrate binding region or coenzyme binding region can be used that interacts with a different substrate or coenzyme specificity and/or affinity than the native ADH. Accordingly, a different set of oxidized/reduced substrates or coenzymes is available as an end-point assay for activation. Alternatively, a heterologous targeting sequence can replace the native targeting sequence. This will result in different subcellular or cellular localization. As a further alternative, sites that are responsible for developmental, temporal, or tissue specificity can be replace by heterologous sites such that the ADH can be detected under conditions of specific developmental, temporal, or tissue-specific expression.

The ADH polypeptides are also useful in competition binding assays in methods designed to discover compounds that interact with the ADH. Thus, a compound is exposed to an ADH polypeptide under conditions that allow the compound to bind or to otherwise interact with the polypeptide. Soluble ADH polypeptide is also added to the mixture. If the test compound interacts with the soluble ADH polypeptide, it decreases the amount of complex formed or activity from the ADH target. This type of assay is particularly useful in cases in which compounds are sought that interact with specific regions of the ADH. Thus, the soluble polypeptide that competes with the target ADH region is designed to contain peptide sequences corresponding to the region of interest.

Another type of competition-binding assay can be used to discover compounds that interact with specific functional sites. As an example, a substrate, such as ethanol, and a candidate compound can be added to a sample of the ADH. Compounds that interact with the ADH at the same site as the ethanol will reduce the amount of complex formed between the ADH and ethanol. Accordingly, it is possible to discover a compound that specifically prevents interaction between the ADH and ethanol. Another example involves adding a candidate compound to a sample of ADH and a coenzyme, such as $NAD^+$. A compound that competes with $NAD^+$ will reduce the coenzyme interaction with ADH and thereby prevent the subsequent interaction with a substrate or the oxidation of the substrate. Accordingly, compounds can be discovered that directly interact with the ADH and compete with various coenzymes and substrates. Such assays can involve any other component that interacts with the ADH.

To perform cell free drug screening assays, it is desirable to immobilize either the ADH, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/ADH fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of ADH-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an ADH-binding target component, such as a coenzyme or a substrate, and a candidate compound are incubated in the ADH-presenting wells and the amount of complex trapped in the well can be quantitated. Methods for detecting such complexes, in addition to those described above for the GST-immobilized complexes, include immunodetection of complexes using antibodies reactive with the ADJ target molecule, or which are reactive with ADH and compete with the target molecule; as well as enzyme-linked assays which rely on detecting an enzymatic activity associated with the target molecule.

Modulators of ADH activity identified according to these drug screening assays can be used to treat a subject with a disorder mediated by ADH, by treating cells that express the ADH. These methods of treatment include the steps of administering the modulators of ADH activity in a pharmaceutical composition as described herein, to a subject in need of such treatment.

The ADHs of the present invention are expressed in various cell types. Tissues and/or cells in which the 21620 ADH is found include, but are not limited to those shown in FIGS. 5 and 6. Tissues in which the gene is highly expressed include brain, colon, kidney, and small intestine. Moderate expression occurs in liver, muscle, and testes. Lower positive expression occurs in the aorta, breast, cervix, esophagus, heart, lung, lymph, ovary, placenta, spleen, thymus, thyroid, and vein. The 21620 ADH is also expressed in the malignant breast, lung, and colon tissue, and in colon metastases to liver.

Hence the ADHs of the present invention are relevant to treating disorders involving these tissues. Of particular interest are malignant breast, liver, colon and liver metastases derived from malignant colon tissue.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders in which the ADH expression is relevant include, but are not limited to, drug/alcohol interactions, susceptibility to alcoholism, alcohol-induced organ injury such as alcoholic liver cirrhosis, first-pass metabolism of alcohol, fetal alcohol syndrome, and alcohol-related cancers including, but not limited to cancers of the esophagus, oral cavity, upper gastrointestinal tract and colorectum.

Furthermore, ADH expression is also relevant to alcohol-induced flushing. Alcohol-induced flushing is characterized by the rapid onset of skin vasodilation of the face, neck and chest regions after consumption of small amounts of alcohol. Tachycardia, headache, nausea, hypotension, and extreme drowsiness are also common symptoms of alcohol-induced flushing. Flush reactions have been correlated with a deficiency or absence of the ADH2 enzyme activity. ADH expression is also relevant in the pathogenesis of male sterility and skin diseases, such as psoriasis. Oxidoreductases have also been implicated in the pathophysiology of neurodegenerative disorders and apoptotic processes related to diseases such as Alzheimer's disease.

The ADH polypeptides are thus useful for treating an ADH-associated disorder characterized by aberrant expression or activity of an ADH. In one embodiment, the method involves administering an agent (e.g., an agent identified by a screening assay described herein), or combination of agents that modulates (e.g., upregulates or downregulates) expression or activity of the protein. In another embodiment, the method involves administering the AHD as therapy to compensate for reduced or aberrant expression or activity of the protein.

Methods for treatment include but are not limited to the use of soluble ADH or fragments of the ADH protein that compete for substrate or coenzyme binding, interfere with subunit interaction, or interfere with the reaction mediated by the ADH polypeptide. These ADHs or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer). In another example, the subject has a disorder mediated by an altered $NADH/NAD^+$ redox potential, as described herein.

In yet another aspect of the invention, the proteins of the invention can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The ADH polypeptides also are useful to provide a target for diagnosing a disease or predisposition to disease mediated by the ADH, including, but not limited to, diseases involving tissues in which the ADHs are expressed as disclosed herein, and particularly in breast, lung, colon, and liver metastases derived from malignant colon tissue. Accordingly, methods are provided for detecting the presence, or levels of, the ADH in a cell, tissue, or organism. The method involves contacting a biological sample with a compound capable of interacting with the ADH such that the interaction can be detected.

One agent for detecting ADH is an antibody capable of selectively binding to ADH. A biological sample includes tissues, cells and biological fluids isolated from a subject, as well as tissues, cells and fluids present within a subject.

The ADH also provides a target for diagnosing active disease, or predisposition to disease, in a patient having a variant ADH. Thus, ADH can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered ADH activity in cell-based or cell-free assay, alteration in substrate or coenzyme binding, altered interaction with ADH subunits, altered rate of substrate oxidation/reduction, altered antibody-binding pattern, altered isoelectric point, direct amino acid sequencing, and any other of the known assay techniques useful for detecting mutations in a protein in general or in an ADH specifically.

In vitro techniques for detection of ADH include enzyme linked immunosorbent assays (ELISAs), Western blots, immunoprecipitations and immunofluorescence. Alternatively, the protein can be detected in vivo in a subject by introducing into the subject a labeled anti-ADH antibody. For example, the antibody can be labeled with a radioactive marker whose presence and location in a subject can be detected by standard imaging techniques. Particularly useful are methods, which detect the allelic variant of the ADH expressed in a subject, and methods, which detect fragments of the ADH in a sample.

The ADH polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the ADH in which one or more of the ADH functions in one population is different from those in another population. The polypeptides thus allow a target to ascertain a genetic predisposition that can affect treatment modality. Thus, in an ADH-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The ADH polypeptides are also useful for monitoring therapeutic effects during clinical trials and other treatment. Thus, the therapeutic effectiveness of an agent that is designed to increase or decrease gene expression, protein levels or ADH activity can be monitored over the course of treatment using the ADH polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the ADH and its variants and fragments. An antibody is considered to selectively bind, even if it also binds to other proteins that are not substantially homologous with the ADH. These other proteins share homology with a fragment or domain of the ADH. This conservation in specific regions gives rise to antibodies that bind to both proteins by virtue of the homologous sequence. In this case, it would be understood that antibody binding to the ADH is still selective.

To generate antibodies, an isolated ADH polypeptide is used as an immunogen to generate antibodies using standard techniques for polyclonal and monoclonal antibody preparation. Either the full-length protein or antigenic peptide fragment can be used. Regions having a high antigenicity index are shown in FIGS. 2, 8, 12, 16, 20 and 21.

Antibodies are preferably prepared from these regions or from discrete fragments in these regions. However, antibodies can be prepared from any region of the peptide as described herein. A preferred fragment produces an antibody that diminishes or completely prevents substrate or coenzyme binding or prevents the oxidation of substrate. Antibodies can be developed against the entire ADH or domains of the ADH as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate an ADH by standard techniques, such as affinity chromatography or immunoprecipitation. The antibodies can facilitate the purification of the natural ADH from cells and recombinantly produced ADH expressed in host cells.

The antibodies are useful to detect the presence of ADH in cells or tissues to determine the pattern of expression of the ADH among various tissues in an organism and over the course of normal development.

The antibodies can be used to detect ADH in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length ADH can be used to identify ADH turnover.

Further, the antibodies can be used to assess ADH expression in disease states such as in active stages of the disease or in an individual with a predisposition toward disease related to ADH function. When a disorder is caused by an inappropriate tissue distribution, developmental expression, or level of expression of the ADH protein, the antibody can be prepared against the normal ADH protein. If a disorder is characterized by a specific mutation in the ADH, antibodies specific for this mutant protein can be used to assay for the presence of the specific mutant ADH. However, intracellularly-made antibodies ("intrabodies") are also encompassed, which would recognize intracellular ADH peptide regions.

The antibodies can also be used to assess normal and aberrant subcellular localization of cells in the various tissues in an organism. Antibodies can be developed against the whole ADH or portions of the ADH.

The diagnostic uses can be applied, not only in genetic testing, but also in monitoring a treatment modality. Accordingly, where treatment is ultimately aimed at correcting ADH expression level or the presence of aberrant ADHs and aberrant tissue distribution or developmental expression, antibodies directed against the ADH or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic ADH can be used to identify individuals that require modified treatment modalities.

The antibodies are also useful as diagnostic tools as an immunological marker for aberrant ADH analyzed by electrophoretic mobility, isoelectric point, tryptic peptide digest, and other physical assays known to those in the art.

The antibodies are also useful for tissue typing. Thus, where a specific ADH has been correlated with expression in a specific tissue, antibodies that are specific for this ADH can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting ADH function, for example, blocking substrate or coenzyme binding or disrupting the oxidation/reduction of substrate.

These uses can also be applied in a therapeutic context in which treatment involves inhibiting ADH function. An antibody can be used, for example, to block coenzyme or substrate binding. Antibodies can be prepared against specific fragments containing sites required for function or against intact ADH associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of an ADH protein in a biological sample. The kit can comprise antibodies such as a labeled or labelable antibody and a compound or agent for detecting ADH in a biological sample; means for determining the amount of ADH in the sample; and means for comparing the amount of ADH in the sample with a standard. The compound or agent can be packaged in a suitable container. The kit can further comprise instructions for using the kit to detect ADH.

Polynucleotides

The nucleotide sequences in SEQ ID NOS:2, 4, 6, 8, and 10, were obtained by sequencing the deposited human cDNA. Accordingly, the sequence of the deposited clones are controlling as to any discrepancies between the two and any reference to the sequences of SEQ ID NOS:2, 4, 6, 8, and 10, includes reference to the sequences of the deposited cDNA.

The specifically disclosed cDNAs comprise the coding region and 5' and 3' untranslated sequences in SEQ ID NOS:2, 4, 6, 8, and 10.

The invention provides isolated polynucleotides encoding the novel ADHs. The term "ADH polynucleotide" or "ADH nucleic acid" refers to the sequences shown in SEQ ID NOS:2, 4, 6, 8, and 10 or in the deposited cDNAs. The term "ADH polynucleotide" or "ADH nucleic acid" further includes variants and fragments of the ADH polynucleotides.

An "isolated" ADH nucleic acid is one that is separated from other nucleic acid present in the natural source of the ADH nucleic acid. Preferably, an "isolated" nucleic acid is free of sequences which naturally flank the ADH nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the ADH nucleic acid is isolated from flanking sequences such that it can be subjected to the specific manipulations described herein, such as recombinant expression, preparation of probes and primers, and other uses specific to the ADH nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The ADH polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The ADH polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

ADH polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

ADH nucleic acid can comprise the nucleotide sequences shown in SEQ ID NOS:2, 4, 6, 8, and 10, corresponding to human the 21620, 33756, 21676, 21612, and 21615 ADH cDNAs, respectfully.

In one embodiment, the ADH nucleic acid comprises only the coding region.

The invention further provides variant ADH polynucleotides, and fragments thereof, that differ from the nucleotide sequences shown in SEQ ID NOS:2, 4, 6, 8, and 10 due to degeneracy of the genetic code and thus encode the same protein as that encoded by the nucleotide sequences shown in SEQ ID NOS:2, 4, 6, 8, and 10.

The invention also provides ADH nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NOS:2, 4, 6, 8, and 10, and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding an ADH that is at least about 60–65%, 65–70%, typically at least about 70–75%, more typically at least about 80–85%, and most typically at least about 90–95% or more homologous to the nucleotide sequence shown in SEQ ID NOS:2, 4, 6, 8, and 10, or a fragment of this sequence. Such nucleic acid molecules can readily be identified as being able to hybridize under stringent conditions, to the nucleotide sequence shown in SEQ ID NOS:2, 4, 6, 8, and 10 or a fragment of the sequence. It is understood that stringent hybridization does not indicate substantial homology where it is due to general homology, such as poly A sequences, or sequences common to all or most proteins, all ADHs, or all short-chain dehydrogenase/reductases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1–6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50–65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:2, 4, 6, 8, and 10 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NOS:2, 4, 6, 8, and 10 or the complement of SEQ ID NOS:2, 4, 6, 8, and 10. In one embodiment, the nucleic acid consists of a portion of the nucleotide sequence of SEQ ID NOS:2, 4, 6, 8, and 10, and the complement of SEQ ID NOS:2, 4, 6, 8, and 10.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, preferably at least about 15, 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

For the 21620 ADH, for example, nucleotide sequences from about 265 to about 300, from about 782 to about 870, from about 1003 to about 1035, and from about 1096 to about 1158 are not disclosed prior to the present invention. The nucleotide sequences from about 1 to about 301 encompasses fragments greater than about 125, 135, 145 or 155 nucleotides; the nucleotide sequences from about 138 to about 1159 encompasses fragments greater than 268, 280, 290, or 300 nucleotides; the nucleotide sequences from about 871 to about 1560 encompasses fragments greater than 265, 275, 285, or 295; and the nucleotide sequences from about 1036 to about 1877 encompasses fragments greater than 266, 275, 285, or 295 nucleotides.

For the 33756ADH, for example, nucleotide sequences from about 66 to about 242 are not disclosed prior to the present invention. The nucleotide sequences from about 1 to about 454 encompass fragments greater than 21, 25, 30, or 35 nucleotides; the nucleotide sequences from about 1 to about 700 encompass fragments greater than 240, 250, 260 or 275 nucleotide; and the nucleotide sequences from about 1 to about 1153 encompass fragments greater than 574, 580, 590 or 600 nucleotides.

For the 21676 ADH, for example, nucleotide sequences from about 1 to about 14, from about 69 to about 94, and from about 206 to about 1699 are not disclosed prior to the present invention. The nucleotide sequences from about 1 to about 206 encompasses fragments greater than 20, 25, 30, 35, 40 or 45 nucleotides.

For the 21612 ADH, for example, nucleotide sequences from about 32 to about 51, from about 679 to about 710, and from about 1525 to about 2535 are not disclosed prior to the present invention. The nucleotide sequences from about 1 to about 678 encompasses fragments greater than 247, 260, 270, or 280 nucleotides and the nucleotide sequences from about 147 to about 2535 encompasses fragments greater than 417, 425, 435, 445 or 455 nucleotides.

For the 21615 ADH, for example, nucleotide sequences from about 538 to about 1615 are not disclosed prior to the present invention. The nucletotide sequence from about nucleotide 1 to about nucleotide 788 encompasses fragments greater than 230, 240, 250 or 260 nucleotides and the nucleotide sequence from about nucleotide 442 to about 1615 encompasses fragments greater than 670, 680, 690 or 700 nucleotides.

Furthermore, the invention provides polynucleotides that comprise a fragment of the full-length ADH polynucleotides. The fragment can be single or double-stranded and can comprise DNA or RNA. The fragment can be derived from either the coding or the non-coding sequence.

In another embodiment an isolated ADH nucleic acid encodes the entire coding region. In another embodiment the isolated ADH nucleic acid encodes a sequence corresponding to the mature protein. For example, the mature form of the 21676 ADH is from about amino acid 16 to the last amino acid. Other fragments include nucleotide sequences encoding the amino acid fragments described herein.

Thus, ADH nucleic acid fragments further include sequences corresponding to the domains described herein, subregions also described, and specific functional sites. ADH nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that an ADH fragment includes any nucleic acid sequence that does not include the entire gene.

The invention also provides ADH nucleic acid fragments that encode epitope bearing regions of the ADH proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NOS:2, 4, 6, 8, and 10 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5'end of the nucleic acid sequence to be amplified and a 3' (downstream) primer that hybridizes with the complement of the sequence to be amplified.

The ADH polynucleotides are thus useful for probes, primers, and in biological assays.

Where the polynucleotides are used to assess ADH properties or functions, such as in the assays described herein, all or less than all of the entire cDNA can be useful. Assays specifically directed to ADH functions, such as assessing agonist or antagonist activity, encompass the use of known fragments. Further, diagnostic methods for assessing ADH function can also be practiced with any fragment, including those fragments that may have been known prior to the invention. Similarly, in methods involving treatment of ADH dysfunction, all fragments are encompassed including those, which may have been known in the art.

The ADH polynucleotides are useful as a hybridization probe for cDNA and genomic DNA to isolate a full-length cDNA and genomic clones encoding the polypeptides described in SEQ ID NOS:1, 3, 5, 7, and 9, and to isolate cDNA and genomic clones that correspond to variants producing the same polypeptides shown in SEQ ID NOS:1, 3, 5, 7, and 9 or the other variants described herein. Variants can be isolated from the same tissue and organism from which the polypeptides shown in SEQ ID NOS:1, 3, 5, 7, and 9, were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the ADH. Accordingly, it could be derived from 5' noncoding regions, the coding region, and 3' noncoding regions.

The nucleic acid probe can be, for example, the full-length cDNA of SEQ ID NOS:2, 4, 6, 8, and 10, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NOS:2, 4, 6, 8, and 10, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell ADHs in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The ADH polynucleotides are also useful as primers for PCR to amplify any given region of an ADH polynucleotide.

The ADH polynucleotides are also useful for constructing recombinant vectors. Such vectors include expression vectors that express a portion of, or all of, the ADH polypeptides. Vectors also include insertion vectors, used to integrate into another polynucleotide sequence, such as into the cellular genome, to alter in situ expression of ADH genes and gene products. For example, an endogenous ADH coding sequence can be replaced via homologous recombination with all or part of the coding region containing one or more specifically introduced mutations.

The ADH polynucleotides are also useful for expressing antigenic portions of the ADH proteins.

The ADH polynucleotides are also useful as probes for determining the chromosomal positions of the ADH polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The ADH polynucleotide probes are also useful to determine patterns of the presence of the gene encoding the ADHs and their variants with respect to tissue distribution, for example, whether gene duplication has occurred and whether the duplication occurs in all or only a subset of tissues. The genes can be naturally occurring or can have been introduced into a cell, tissue, or organism exogenously.

The ADH polynucleotides are also useful for designing ribozymes corresponding to all, or a part, of the mRNA produced from genes encoding the polynucleotides described herein.

The ADH polynucleotides are also useful for constructing host cells expressing a part, or all, of the ADH polynucleotides and polypeptides.

The ADH polynucleotides are also useful for constructing transgenic animals expressing all, or a part, of the ADH polynucleotides and polypeptides.

The ADH polynucleotides are also useful for making vectors that express part, or all, of the ADH polypeptides.

The ADH polynucleotides are also useful as hybridization probes for determining the level of ADH nucleic acid expression. Accordingly, the probes can be used to detect the presence of, or to determine levels of, ADH nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the ADH genes.

Alternatively, the probe can be used in an in situ hybridization context to assess the position of extra copies of the ADH genes, as on extrachromosomal elements or as integrated into chromosomes in which the ADH gene is not normally found, for example as a homogeneously staining region.

These uses are relevant for diagnosis of disorders involving an increase or decrease in ADH expression relative to normal, such as a proliferative disorder or a differentiative or developmental disorder.

Tissues and/or cells in which the 21620 ADH is expressed are shown in FIGS. 5 and 6 and are described above herein. As such, the gene is particularly relevant for the treatment of disorders involving these tissues.

Furthermore, disorders in which ADH expression is relevant are disclosed herein above.

Thus, the present invention provides a method for identifying a disease or disorder associated with aberrant expression or activity of ADH nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the ADH, such as by measuring the level of an ADH-encoding nucleic acid in a sample of cells from a subject e.g., mRNA or genomic DNA, or determining if the ADH gene has been mutated.

Nucleic acid expression assays are useful for drug screening to identify compounds that modulate ADH nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the ADH gene. The method typically includes assaying the ability of the compound to modulate the expression of the ADH nucleic acid and thus identifying a compound that can be used to treat a disorder characterized by undesired ADH nucleic acid expression.

The assays can be performed in cell-based and cell-free systems. Cell-based assays include cells naturally expressing the ADH nucleic acid or recombinant cells genetically engineered to express specific nucleic acid sequences.

Alternatively, candidate compounds can be assayed in vivo in patients or in transgenic animals.

The assay for ADH nucleic acid expression can involve direct assay of nucleic acid levels, such as mRNA levels, or on collateral compounds involved in the ADH catalized reaction (such as oxidized/reduced products, $NAD^+$/NADH ratio, or components of the retinoic and signaling pathway). Further, the expression of genes that are up- or down-regulated in response to the ADH signal pathway can also be assayed. In this embodiment the regulatory regions of these genes can be operably linked to a reporter gene such as luciferase.

Thus, modulators of ADH gene expression can be identified in a method wherein a cell is contacted with a candidate compound and the expression of mRNA determined. The level of expression of ADH mRNA in the presence of the candidate compound is compared to the level of expression of ADH mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate ADH nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid. Disorders that the gene is particularly relevant for treating have been disclosed herein above.

Alternatively, a modulator for ADH nucleic acid expression can be a small molecule or drug identified using the screening assays described herein as long as the drug or small molecule inhibits the ADH nucleic acid expression.

The ADH polynucleotides are also useful for monitoring the effectiveness of modulating compounds on the expression or activity of the ADH gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The ADH polynucleotides are also useful in diagnostic assays for qualitative changes in ADH nucleic acid, and particularly in qualitative changes that lead to pathology. The polynucleotides can be used to detect mutations in ADH genes and gene expression products such as mRNA. The polynucleotides can be used as hybridization probes to detect naturally-occurring genetic mutations in the ADH gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the ADH gene associated with a dysfunction provides a diagnostic tool for an active disease or susceptibility to disease when the disease results from overexpression, underexpression, or altered expression of an ADH.

Mutations in the ADH gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) PNAS 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an ADH gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant ADH gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) PNAS 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The ADH polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the ADH gene that results in altered affinity for a coenzyme could result in an excessive or decreased drug effect with standard concentrations of the coenzyme that activates the ADH. Accordingly, the ADH polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The ADH polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The ADH polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the ADH sequence can be used to provide an alternative technique, which determines the actual DNA sequence of selected fragments in the genome of an individual. Thus, the ADH sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The ADH sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The ADH polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The ADH polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The ADH polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of ADH probes can be used to identify tissue by species and/or by organ type.

In a similar fashion, these primers and probes can be used to screen tissue culture for contamination (i.e. screen for the presence of a mixture of different types of cells in a culture).

Alternatively, the ADH polynucleotides can be used directly to block transcription or translation of ADH gene sequences by means of antisense or ribozyme constructs. Thus, in a disorder characterized by abnormally high or undesirable ADH gene expression, nucleic acids can be directly used for treatment.

The ADH polynucleotides are thus useful as antisense constructs to control ADH gene expression in cells, tissues, and organisms. A DNA antisense polynucleotide is designed to be complementary to a region of the gene involved in transcription, preventing transcription and hence production of ADH protein. An antisense RNA or DNA polynucleotide would hybridize to the mRNA and thus block translation of mRNA into ADH protein.

Examples of antisense molecules useful to inhibit nucleic acid expression include antisense molecules complementary to a fragment of the 5' untranslated region of SEQ ID NOS:2, 4, 6, 8, and 10, which also includes the start codon and antisense molecules which are complementary to a fragment of the 3' untranslated region of SEQ ID NOS:2, 4, 6, 8, and 10.

Alternatively, a class of antisense molecules can be used to inactivate mRNA in order to decrease expression of an ADH nucleic acid. Accordingly, these molecules can treat a disorder characterized by abnormal or undesired ADH nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the ADH protein.

The ADH polynucleotides also provide vectors for gene therapy in patients containing cells that are aberrant in ADH gene expression. Thus, recombinant cells, which include the patient's cells that have been engineered ex vivo and returned to the patient, are introduced into an individual where the cells produce the desired ADH protein to treat the individual.

The invention also encompasses kits for detecting the presence of an ADH nucleic acid in a biological sample. For example, the kit can comprise reagents such as a labeled or labelable nucleic acid or agent capable of detecting ADH nucleic acid in a biological sample; means for determining the amount of ADH nucleic acid in the sample; and means for comparing the amount of ADH nucleic acid in the sample with a standard. The compound or agent can be packaged in a suitable container. The kit can further comprise instructions for using the kit to detect ADH mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled-artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the ADH polynucleotides. The term "vector" refers to a vehicle, preferably a nucleic acid molecule that can transport the ADH polynucleotides. When the vector is a nucleic acid molecule, the ADH polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the ADH polynucleotides. Alternatively, the vector may integrate into the host cell genome and produce additional copies of the ADH polynucleotides when the host cell replicates.

The invention provides vectors for the maintenance (cloning vectors) or vectors for expression (expression vectors) of the ADH polynucleotides. The vectors can function in procaryotic or eukaryotic cells or in both (shuttle vectors).

Expression vectors contain cis-acting regulatory regions that are operably linked in the vector to the ADH polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the ADH polynucleotides from the vector. Alternatively, a trans-acting factor may be supplied by the host cell. Finally, a trans-acting factor can be produced from the vector itself.

It is understood, however, that in some embodiments, transcription and/or translation of the ADH polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd ed., Cold Spring Harbor Laboratory Press, Cold Spring Harbor, N.Y.).

A variety of expression vectors can be used to express an ADH polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning. A Laboratory Manual* 2nd ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The ADH polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurizim*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the ADH polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5

(Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E coli*. (Wada et al. (1992) *Nucleic Acids Res.* 20:2111–2118).

The ADH polynucleotides can also be expressed by expression vectors that are operative in yeast. Examples of vectors for expression in yeast e.g., *S. cerevisiae* include pYepSec1 (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The ADH polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the ADH polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed, Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the ADH polynucleotides can be introduced either alone or with other polynucleotides that are not related to the ADH polynucleotides such as those providing trans-acting factors for expression vectors. When more than one vector is introduced into a cell, the vectors can be introduced independently, co-introduced or joined to the ADH polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the ADH polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing ADH proteins or polypeptides that can be further purified to produce desired amounts of ADH protein or fragments. Thus, host cells containing expression vectors are useful for polypeptide production.

Host cells are also useful for conducting cell-based assays involving the ADH or ADH fragments. Thus, a recombinant host cell expressing a native ADH is useful to assay for compounds that stimulate or inhibit ADH function. This includes gene expression at the level of transcription or translation, interactions with coenzymes, substrates or ADH subunits, and catalysis of substrate oxidation/reduction.

Host cells are also useful for identifying ADH mutants in which these functions are affected. If the mutants naturally occur and give rise to a pathology, host cells containing the mutations are useful to assay compounds that have a desired effect on the mutant ADH (for example, stimulating or inhibiting function) which may not be indicated by their effect on the native ADH.

Recombinant host cells are also useful for expressing the chimeric polypeptides described herein to assess compounds that activate or suppress activation by means of a heterologous domain, segment, site, and the like, as disclosed herein.

Further, mutant ADHs can be designed in which one or more of the various functions is engineered to be increased or decreased (e.g., coenzyme, substrate, or ADH subunits) and used to augment or replace ADH proteins in an individual. Thus, host cells can provide a therapeutic benefit by replacing an aberrant ADH or providing an aberrant ADH that provides a therapeutic result. In one embodiment, the cells provide ADHs that are abnormally active.

In another embodiment, the cells provide ADH that are abnormally inactive. These ADHs can compete with endogenous ADHs in the individual.

In another embodiment, cells expressing ADHs that are not catalytically active, are introduced into an individual in order to compete with endogenous ADHs for substrate, coenzymes or ADH subunits. For example, in the case in which excessive amounts of an ADH substrate is part of a treatment modality, it may be necessary to inactivate this molecule at a specific point in treatment. Providing cells that compete for the molecule, but which cannot be affected by ADH activation would be beneficial.

Homologously recombinant host cells can also be produced that allow the in situ alteration of endogenous ADH polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat. No. 5,641,670. Briefly, specific polynucleotide sequences corresponding to the ADH polynucleotides or sequences proximal or distal to an ADH gene are allowed to integrate into a host cell genome by homologous recombination where expression of the gene can be affected. In one embodiment, regulatory sequences are introduced that either increase or decrease expression of an endogenous sequence. Accordingly, an ADH protein can be produced in a cell not normally producing it. Alternatively, increased expression of ADH protein can be effected in a cell normally producing the protein at a specific level. Further, expression can be decreased or eliminated by introducing a specific regulatory sequence. The regulatory sequence can be heterologous to the ADH protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant ADH proteins. Such mutations could be introduced, for example, into the specific functional regions such as the substrate-binding site.

In one embodiment, the host cell can be a fertilized oocyte or embryonic stem cell that can be used to produce a transgenic animal containing the altered ADH gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous ADH gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cell: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an ADH protein and identifying and evaluating modulators of ADH protein activity.

Other examples of transgenic animals include non-human primates, sheep, dogs, cows, goats, chickens, and amphibians.

In one embodiment, a host cell is a fertilized oocyte or an embryonic stem cell into which ADH polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the ADH nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the ADH protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) PNAS 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect substrate and coenzyme binding, and oxidation of the substrate may not be evident from in vitro cell-free or cell-based assays. Accordingly, it is useful to provide non-human transgenic animals to assay in vivo ADH function, including substrate and coenzyme interactions and substrate oxidation. Similar methods could be used to determine the effect of specific mutant ADHs and the effect of chimeric ADHs on such enzyme functions. It is also possible to assess the effect of null mutations, that is mutations that substantially or completely eliminate one or more ADH functions.

In general, methods for producing transgenic animals include introducing a nucleic acid sequence according to the present invention, the nucleic acid sequence capable of expressing the ADH protein in a transgenic animal, into a cell in culture or in vivo. When introduced in vivo, the nucleic acid is introduced into an intact organism such that one or more cell types and, accordingly, one or more tissue types, express the nucleic acid encoding the ADH protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The ADH nucleic acid molecules, protein (such as an extracellular loop), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™

(BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ADH protein or anti-ADH antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule comprising a nucleotide sequence selected from the group consisting of:
   a) the nucleotide sequence set forth in SEQ ID NO:8;
   b) the nucleotide sequence of the cDNA insert of the plasmid deposited with ATCC as Patent Deposit Number PTA-2170;
   c) a nucleotide sequence encoding the amino acid sequence set forth in SEQ ID NO:7;
   d) a nucleotide sequence encoding the amino acid sequence encoded by the cDNA insert of the plasmid deposited with ATCC as Patent Deposit Number PTA-2170; and
   e) a nucleotide sequence complementary to a nucleotide sequence of a), b), c), or d).

2. The nucleic acid molecule of claim 1, further comprising vector nucleic acid sequences.

3. The nucleic acid molecule of claim 1 further comprising nucleic acid sequences encoding a heterologous polypeptide.

4. A host cell which contains the nucleic acid molecule of claim 1.

5. The host cell of claim 4 which is a mammalian host cell.

6. A nonhuman mammalian host cell containing the nucleic acid molecule of claim 1.

7. A method for detecting the presence of a nucleic acid molecule of claim 1 in a sample, said method comprising the steps of contacting the sample with a nucleic acid probe which selectively hybridizes to the nucleic acid molecule and determining whether the nucleic acid probe binds to the nucleic acid molecule in the sample; wherein said nucleic acid probe is selected from the group consisting of:
   a) the nucleotide sequence set forth in SEQ ID NO:8;
   b) the nucleotide sequence of a fragment of the nucleotide sequence set for in SEQ ID NO:8, wherein said fragment comprises at least 417 contiguous nucleotides of the nucleotide sequence set forth in SEQ ID NO:8;
   c) a nucleotide sequence having at least 70% sequence identity to the nucleotide sequence set forth in SEQ ID NO:8; and
   d) a nucleotide sequence complementary to a nucleotide sequence of a), b), or c).

8. The method of claim 7, wherein the sample comprises mRNA molecules.

9. A kit for use in the method of claim 7, wherein said kit comprises at least one nucleic acid probe of claim 7 and instructions for use in the method of claim 7.

10. An isolated nucleic acid molecule having a nucleotide selected from the group consisting of:
   a) a nucleotide sequence encoding a polypeptide having dehydrogenase activity, wherein said nucleotide sequence has at least 70% sequence identity with the nucleotide sequence set forth in SEQ ID NO:8; and
   b) a nucleotide sequence complementary to the nucleotide sequence of a).

11. The nucleic acid molecule of claim 10, wherein said nucleotide sequence is selected from the group consisting of:
   a) a nucleotide sequence encoding a polypeptide having dehydrogenase activity, wherein said nucleotide sequence has at least 80% sequence identity with the nucleotide sequence set forth in SEQ ID NO:8; and
   b) a nucleotide sequence complementary to the nucleotide sequence of a).

12. The nucleic acid molecule of claim 11, wherein said nucleotide sequence is selected from the group consisting of:
   a) a nucleotide sequence encoding a polypeptide having dehydrogenase activity, wherein said nucleotide sequence has at least 90% sequence identity with the nucleotide sequence set forth in SEQ ID NO:8; and
   b) a nucleotide sequence complementary to the nucleotide sequence of a).

13. An isolated nucleic acid molecule comprising a nucleotide sequence selected from the group consisting of:
   a) a nucleotide sequence encoding a polypeptide having dehydrogenase activity, wherein the complement of said nucleotide sequence hybridizes under stringent conditions to the nucleotide sequence set forth in SEQ ID NO:8, said stringent conditions comprising hybridization at about 45° C., followed by at least one wash in 0.2×SSC/0.1% SDS at 65° C.; and
   b) a nucleotide sequence complementary to the nucleotide sequence of a).

14. An isolated nucleic acid molecule comprising a nucleotide sequence selected from the group consisting of:
   a) a nucleotide sequence encoding a fragment of the amino acid sequence set forth in SEQ ID NO:7, wherein said fragment has dehydrogenase activity and consists of at least 139 contiguous amino acids of SEQ ID NO:7; and
   b) a nucleotide sequence encoding a fragment of the amino acid sequence encoded by the cDNA insert of the plasmid deposited with ATCC as Patent Deposit Number PTA-2170, wherein the fragment has dehydrogenase activity and consists of at least 139 contiguous amino acids of the amino acid sequence encoded by the cDNA insert of the plasmid deposited with ATCC as Patent Deposit Number PTA-2170; and
   c) a nucleotide sequence complementary to the nucleotide sequence of a) or b).

15. The nucleic acid molecule of claim 10 further comprising vector nucleic acid sequences.

16. The nucleic acid molecule of claim 10 further comprising nucleic acid sequences encoding a heterologous polypeptide.

17. A host cell which contains the nucleic acid molecule of claim 10.

18. The host cell of claim 17, wherein said host cell is a mammalian host cell.

19. A nonhuman mammalian host cell containing the nucleic acid molecule of claim 10.

20. A method for detecting the presence of a nucleic acid molecule of claim 10 in a sample, said method comprising the steps of contacting the sample with a nucleic acid probe which selectively hybridizes to the nucleic acid molecule and determining whether the nucleic acid probe or primer binds to a nucleic acid molecule in the sample; wherein said nucleic acid probe is selected from the group consisting of:
   a) the nucleotide sequence set forth in SEQ ID NO:8;
   b) the nucleotide sequence of a fragment of the nucleotide sequence set for in SEQ ID NO:8, wherein said fragment comprises at least 417 contiguous nucleotides of the nucleotide sequence set forth in SEQ ID NO:8;
   c) a nucleotide sequence having at least 70% sequence identity to the nucleotide sequence set forth in SEQ ID NO:8; and
   d) a nucleotide sequence complementary to a nucleotide sequence of a), b), or c).

21. The method of claim 20, wherein the sample comprises mRNA molecules.

22. A kit for use in the method of claim 20, wherein said kit comprises at least one nucleic acid probe of claim 20 and instructions for use in the method of claim 20.

23. A method for producing a polypeptide, said method comprising culturing a host cell containing a nucleic acid molecule of claim 1 under conditions in which the polypeptide encoded by the nucleic acid molecule is expressed.

24. A method for producing a polypeptide, said method comprising culturing a host cell containing a nucleic acid molecule of claim 10 under conditions in which the polypeptide encoded by the nucleic acid molecule is expressed.

25. A method for producing a polypeptide, said method comprising culturing a host cell containing a nucleic acid molecule of claim 12 under conditions in which the polypeptide encoded by the nucleic acid molecule is expressed.

26. A method for producing a polypeptide said method comprising culturing a host cell containing a nucleic acid molecule of claim 13 under conditions in which the polypeptide encoded by the nucleic acid molecule is expressed.

* * * * *

SEQUENCE LISTING

<160> NUMBER OF SEQ ID NOS: 10

<210> SEQ ID NO 1
<211> LENGTH: 260
<212> TYPE: PRT
<213> ORGANISM: Homo sapiens

<400> SEQUENCE: 1

Met Ala Arg Pro Gly Met Glu Arg Trp Arg Asp Arg Leu Ala Leu Val
1               5                   10                  15

Thr Gly Ala Ser Gly Gly Ile Gly Ala Ala Val Ala Arg Ala Leu Val
            20                  25                  30

Gln Gln Gly Leu Lys Val Val Gly Cys Ala Arg Thr Val Gly Asn Ile
        35                  40                  45

Glu Glu Leu Ala Ala Glu Cys Lys Ser Ala Gly Tyr Pro Gly Thr Leu
    50                  55                  60

Ile Pro Tyr Arg Cys Asp Leu Ser Asn Glu Glu Asp Ile Leu Ser Met
65                  70                  75                  80

Phe Ser Ala Ile Arg Ser Gln His Ser Gly Val Asp Ile Cys Ile Asn
                85                  90                  95

-continued

```
            Asn Ala Gly Leu Ala Arg Pro Asp Thr Leu Leu Ser Gly Ser Thr Ser
                        100                 105                 110

Gly Trp Lys Asp Met Phe Asn Val Asn Val Leu Ala Leu Ser Ile Cys
                    115                 120                 125

Thr Arg Glu Ala Tyr Gln Ser Met Lys Glu Arg Asn Val Asp Asp Gly
                130                 135                 140

His Ile Ile Asn Ile Asn Ser Met Ser Gly His Arg Val Leu Pro Leu
            145                 150                 155                 160

Ser Val Thr His Phe Tyr Ser Ala Thr Lys Tyr Ala Val Thr Ala Leu
                            165                 170                 175

Thr Glu Gly Leu Arg Gln Glu Leu Arg Glu Ala Gln Thr His Ile Arg
                        180                 185                 190

Ala Thr Cys Ile Ser Pro Gly Val Val Glu Thr Gln Phe Ala Phe Lys
                    195                 200                 205

Leu His Asp Lys Asp Pro Glu Lys Ala Ala Ala Thr Tyr Glu Gln Met
                210                 215                 220

Lys Cys Leu Lys Pro Glu Asp Val Ala Glu Ala Val Ile Tyr Val Leu
            225                 230                 235                 240

Ser Thr Pro Ala His Ile Gln Ile Gly Asp Ile Gln Met Arg Pro Thr
                            245                 250                 255

Glu Gln Val Thr
                        260

<210> SEQ ID NO 2
<211> LENGTH: 1909
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 21620 ADH
<220> FEATURE:
<221> NAME/KEY: CDS
<222> LOCATION: (421)...(1203)
<221> NAME/KEY: misc_feature
<222> LOCATION: (1)...(1909)
<223> OTHER INFORMATION: n = A,T,C or G

<400> SEQUENCE: 2
tacttagact cagccggctt ttccacgctt tgcctgaccc tgctttgctc aactgtacgt      60
cttgtttcgt tttctgttct gcgccgttac agatccaagc tctgaaaaac cagaaagtta    120
actggtaagt ttagtctttt tgtcttttat ttcaggtccc ggatccggtg atccaaatct    180
aagaactgct cctcagtgag tgttgccttt acttctaggc ctgtacggaa gtgttacttc    240
tgctctaaaa gctgcggaat tctaatacga ctcactatag ggagtcgacc cacgcgtccg    300
gggtctaggc gcggatcgga cccaagcagg tcggcggcgg cggcaggaga gcggccgggc    360
gtcagctcct cgaccccgt gtcgggctag tccagcgagg cggacgggcg gcgtgggccc     420 atg gcc agg ccc ggc atg gag cgg tgg cgc gac cgg ctg gcg ctg gtg     468
Met Ala Arg Pro Gly Met Glu Arg Trp Arg Asp Arg Leu Ala Leu Val
  1               5                  10                  15 acg ggg gcc tcg ggg ggc atc ggc gcg gcc gtg gcc cgg gcc ctg gtc     516
Thr Gly Ala Ser Gly Gly Ile Gly Ala Ala Val Ala Arg Ala Leu Val
                 20                  25                  30 cag cag gga ctg aag gtg gtg ggc tgc gcc cgc act gtg ggc aac atc     564
Gln Gln Gly Leu Lys Val Val Gly Cys Ala Arg Thr Val Gly Asn Ile
             35                  40                  45
```

-continued

| | |
|---|---|
| gag gag ctg gct gct gaa tgt aag agt gca ggc tac ccc ggg act ttg<br>Glu Glu Leu Ala Ala Glu Cys Lys Ser Ala Gly Tyr Pro Gly Thr Leu<br>50                  55                  60 | 612 |
| atc ccc tac aga tgt gac cta tca aat gaa gag gac atc ctc tcc atg<br>Ile Pro Tyr Arg Cys Asp Leu Ser Asn Glu Glu Asp Ile Leu Ser Met<br>65                  70                  75                  80 | 660 |
| ttc tca gct atc cgt tct cag cac agc ggt gta gac atc tgc atc aac<br>Phe Ser Ala Ile Arg Ser Gln His Ser Gly Val Asp Ile Cys Ile Asn<br>                    85                  90                  95 | 708 |
| aat gct ggc ttg gcc cgg cct gac acc ctg ctc tca ggc agc acc agt<br>Asn Ala Gly Leu Ala Arg Pro Asp Thr Leu Leu Ser Gly Ser Thr Ser<br>            100                 105                 110 | 756 |
| ggt tgg aag gac atg ttc aat gtg aac gtg ctg gcc ctc agc atc tgc<br>Gly Trp Lys Asp Met Phe Asn Val Asn Val Leu Ala Leu Ser Ile Cys<br>       115                 120                 125 | 804 |
| aca cgg gaa gcc tac cag tcc atg aag gag cgg aat gtg gac gat ggg<br>Thr Arg Glu Ala Tyr Gln Ser Met Lys Glu Arg Asn Val Asp Asp Gly<br>130                 135                 140 | 852 |
| cac atc att aac atc aat agc atg tct ggc cac cga gtg tta ccc ctg<br>His Ile Ile Asn Ile Asn Ser Met Ser Gly His Arg Val Leu Pro Leu<br>145                 150                 155                 160 | 900 |
| tct gtg acc cac ttc tat agt gcc acc aag tat gcc gtc act gcg ctg<br>Ser Val Thr His Phe Tyr Ser Ala Thr Lys Tyr Ala Val Thr Ala Leu<br>                    165                 170                 175 | 948 |
| aca gag gga ctg agg caa gag ctt cgg gag gcc cag acc cac atc cga<br>Thr Glu Gly Leu Arg Gln Glu Leu Arg Glu Ala Gln Thr His Ile Arg<br>            180                 185                 190 | 996 |
| gcc acg tgc atc tct cca ggt gtg gtg gag aca caa ttc gcc ttc aaa<br>Ala Thr Cys Ile Ser Pro Gly Val Val Glu Thr Gln Phe Ala Phe Lys<br>       195                 200                 205 | 1044 |
| ctc cac gac aag gac cct gag aag gca gct gcc acc tat gag caa atg<br>Leu His Asp Lys Asp Pro Glu Lys Ala Ala Ala Thr Tyr Glu Gln Met<br>210                 215                 220 | 1092 |
| aag tgt ctc aaa ccc gag gat gtg gcc gag gct gtt atc tac gtc ctc<br>Lys Cys Leu Lys Pro Glu Asp Val Ala Glu Ala Val Ile Tyr Val Leu<br>225                 230                 235                 240 | 1140 |
| agc act ccc gca cac atc cag att gga gac atc cag atg agg ccc acg<br>Ser Thr Pro Ala His Ile Gln Ile Gly Asp Ile Gln Met Arg Pro Thr<br>                    245                 250                 255 | 1188 |
| gag cag gtg acc tag tgactgtggg agctcctcct tccctcccca cccttcatgg<br>Glu Gln Val Thr<br>            260 | 1243 |
| cttgcctcct gcctctggat tttaggtgtt gatttctgga tcacgggata ccacttcctg | 1303 |
| tccacacccc gaccagggc tagaaaattt gtttgagatt tttatatcat cttgtcaaat | 1363 |
| tgcttcagtt gtaaatgtga aaaatgggct ggggaaagga ggtggtgtcc ctaattgttt | 1423 |
| tacttgttaa cttgttcttg tgcccctggg cacttggcct ttgtctgctc tcagtgtctt | 1483 |
| cccttttgaca tgggaaagga gttgtggcca aaatccccat cttcttgcac ctcaacgtct | 1543 |
| gtggctyang ggctggggtg gcagagggag gccttcacct tatatctgtg ttgttatcca | 1603 |
| gggctccaga cttcctcctc tgcctgcccc actgcacccct ctccccctta tctatctcct | 1663 |
| tctcggctcc ccagcccagt cttggcttct tgtcccctcc tggggtcatc cctccactct | 1723 |
| gactctgact atggcagcag aacaccaggg cctggcccag tggatttcat ggtgatcatt | 1783 |
| aaaaagaaa aatcgcaacc aaaaaaaaaa aaaaagggc gggccgctag actagtytag | 1843 |
| agaaaaaacc tcccacacct cccybdamm ytkacgccgn acgcnanggg ggcaatcaag | 1903 |
| gacgct | 1909 |

-continued

```
<210> SEQ ID NO 3
<211> LENGTH: 260
<212> TYPE: PRT
<213> ORGANISM: Homo sapiens

<400> SEQUENCE: 3
```

Met Glu Lys Cys Glu Ala Ala Lys Asp Ile Arg Gly Glu Thr Leu
 1               5                  10                  15

Asn His His Val Asn Ala Arg His Leu Asp Leu Ala Ser Leu Lys Ser
             20                  25                  30

Ile Arg Glu Phe Ala Ala Lys Ile Ile Glu Glu Glu Arg Val Asp
         35                  40                  45

Ile Leu Ile Asn Asn Ala Gly Val Met Arg Cys Pro His Trp Thr Thr
 50                  55                  60

Glu Asp Gly Phe Glu Met Gln Phe Gly Val Asn His Leu Gly His Phe
 65                  70                  75                  80

Leu Leu Thr Asn Leu Leu Asp Lys Leu Lys Ala Ser Ala Pro Ser
                 85                  90                  95

Arg Ile Ile Asn Leu Ser Ser Leu Ala His Val Ala Gly His Ile Asp
                100                 105                 110

Phe Asp Asp Leu Asn Trp Gln Thr Arg Lys Tyr Asn Thr Lys Ala Ala
            115                 120                 125

Tyr Cys Gln Ser Lys Leu Ala Ile Val Leu Phe Thr Lys Glu Leu Ser
130                 135                 140

Arg Arg Leu Gln Gly Ser Gly Val Thr Val Asn Ala Leu His Pro Gly
145                 150                 155                 160

Val Ala Arg Thr Glu Leu Gly Arg His Thr Gly Ile His Gly Ser Thr
                165                 170                 175

Phe Ser Ser Thr Thr Leu Gly Pro Ile Phe Trp Leu Leu Val Lys Ser
            180                 185                 190

Pro Glu Leu Ala Ala Gln Pro Ser Thr Tyr Leu Ala Val Ala Glu Glu
        195                 200                 205

Leu Ala Asp Val Ser Gly Lys Tyr Phe Asp Gly Leu Lys Gln Lys Ala
210                 215                 220

Pro Ala Pro Glu Ala Glu Asp Glu Glu Val Ala Arg Arg Leu Trp Ala
225                 230                 235                 240

Glu Ser Ala Arg Leu Val Gly Leu Glu Ala Pro Ser Val Arg Glu Gln
                245                 250                 255

Pro Leu Pro Arg
            260

```
<210> SEQ ID NO 4
<211> LENGTH: 1153
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 33756 ADH
<220> FEATURE:
<221> NAME/KEY: CDS
<222> LOCATION: (265)...(1047)
<221> NAME/KEY: misc_feature
<222> LOCATION: (1)...(1153)
<223> OTHER INFORMATION: n = A,T,C or G

<400> SEQUENCE: 4
``` ccgcgcccg ccctcgcagc ccanntncgg acgcgggccc agccgcgcct gcgcttccgc    60
tcgcctgtgg ctgcaannag cgcgctcttc ctcggagcta cccaggcggc tggtgtagca   120

-continued

```
gcaagctccg cgccgacccc tgacgcctga cgcctgtccc cggcccggca tgagccgcta      180
cctgctgccg ctgtcggcgc tgggcacggt agcaggcgct cgccgtgctg ctcaagaggc      240
aacatcatcc tggcctgccg agac atg gag aag tgt gag gcg gca gca aag        291
                          Met Glu Lys Cys Glu Ala Ala Ala Lys
                           1               5 gac atc cgc ggg gag acc ctc aat cac cat gtc aac gcc cgg cac ctg        339
Asp Ile Arg Gly Glu Thr Leu Asn His His Val Asn Ala Arg His Leu
 10              15                  20                  25 gac ttg gct tcc ctc aag tct atc cga gag ttt gca gca aag atc att        387
Asp Leu Ala Ser Leu Lys Ser Ile Arg Glu Phe Ala Ala Lys Ile Ile
             30                  35                  40 gaa gag gag gag cga gtg gac att cta atc aac aac gcg ggt gtg atg        435
Glu Glu Glu Glu Arg Val Asp Ile Leu Ile Asn Asn Ala Gly Val Met
             45                  50                  55 cgg tgc ccc cac tgg acc acc gag gac ggc ttc gag atg cag ttt ggc        483
Arg Cys Pro His Trp Thr Thr Glu Asp Gly Phe Glu Met Gln Phe Gly
 60                  65                  70 gtt aac cac ctg ggt cac ttt ctc ttg aca aac ttg ctg ctg gac aag        531
Val Asn His Leu Gly His Phe Leu Leu Thr Asn Leu Leu Leu Asp Lys
 75                  80                  85 ctg aaa gcc tca gcc cct tcg cgg atc atc aac ctc tcg tcc ctg gcc        579
Leu Lys Ala Ser Ala Pro Ser Arg Ile Ile Asn Leu Ser Ser Leu Ala
 90                  95                 100                 105 cat gtt gct ggg cac ata gac ttt gac gac ttg aac tgg cag acg agg        627
His Val Ala Gly His Ile Asp Phe Asp Asp Leu Asn Trp Gln Thr Arg
                110                 115                 120 aag tat aac acc aaa gcc gcc tac tgc cag agc aag ctc gcc atc gtc        675
Lys Tyr Asn Thr Lys Ala Ala Tyr Cys Gln Ser Lys Leu Ala Ile Val
            125                 130                 135 ctc ttc acc aag gag ttg agc cgg cgg ctg caa ggc tct ggt gtg act        723
Leu Phe Thr Lys Glu Leu Ser Arg Arg Leu Gln Gly Ser Gly Val Thr
            140                 145                 150 gtc aac gcc ctg cac ccc ggc gtg gcc agg aca gag ctg ggc aga cac        771
Val Asn Ala Leu His Pro Gly Val Ala Arg Thr Glu Leu Gly Arg His
155                 160                 165 acg ggc atc cat ggc tcc acc ttc tcc agc acc aca ctc ggg ccc atc        819
Thr Gly Ile His Gly Ser Thr Phe Ser Ser Thr Thr Leu Gly Pro Ile
170                 175                 180                 185 ttc tgg ctg ctg gtc aag agc ccc gag ctg gcc gcc cag ccc agc aca        867
Phe Trp Leu Leu Val Lys Ser Pro Glu Leu Ala Ala Gln Pro Ser Thr
                190                 195                 200 tac ctg gcc gtg gcg gag gaa ctg gcg gat gtt tcc gga aag tac ttc        915
Tyr Leu Ala Val Ala Glu Glu Leu Ala Asp Val Ser Gly Lys Tyr Phe
            205                 210                 215 gat gga ctc aaa cag aag gcc ccg gcc ccc gag gct gag gat gag gag        963
Asp Gly Leu Lys Gln Lys Ala Pro Ala Pro Glu Ala Glu Asp Glu Glu
        220                 225                 230 gtg gcc cgg agg ctt tgg gct gaa agt gcc cgc ctg gtg ggc tta gag       1011
Val Ala Arg Arg Leu Trp Ala Glu Ser Ala Arg Leu Val Gly Leu Glu
235                 240                 245 gct ccc tct gtg agg gag cag ccc ctc ccc aga taa cctctggagc            1057
Ala Pro Ser Val Arg Glu Gln Pro Leu Pro Arg
250                 255                 260 agatttgaaa gccaggatgg cgcctccaga ccgaggacag ctgtccgcca tgcccgcagc     1117
ttcctggcac tacctgagcc gggagaccca ggactg                               1153
```

```
<210> SEQ ID NO 5
<211> LENGTH: 331
<212> TYPE: PRT
<213> ORGANISM: Homo sapiens

<400> SEQUENCE: 5

Met Ser Arg Tyr Leu Leu Pro Leu Ser Ala Leu Gly Thr Val Ala Gly
 1               5                  10                  15

Ala Ala Val Leu Leu Lys Asp Tyr Val Thr Gly Gly Ala Cys Pro Ser
            20                  25                  30

Lys Ala Thr Ile Pro Gly Lys Thr Val Ile Val Thr Gly Ala Asn Thr
        35                  40                  45

Gly Ile Gly Lys Gln Thr Ala Leu Glu Leu Ala Arg Arg Gly Gly Asn
    50                  55                  60

Ile Ile Leu Ala Cys Arg Asp Met Glu Lys Cys Glu Ala Ala Ala Lys
65                  70                  75                  80

Asp Ile Arg Gly Glu Thr Leu Asn His His Val Asn Ala Arg His Leu
                85                  90                  95

Asp Leu Ala Ser Leu Lys Ser Ile Arg Glu Phe Ala Ala Lys Ile Ile
            100                 105                 110

Glu Glu Glu Glu Arg Val Asp Ile Leu Ile Asn Asn Ala Gly Val Met
        115                 120                 125

Arg Cys Pro His Trp Thr Thr Glu Asp Gly Phe Glu Met Gln Phe Gly
    130                 135                 140

Val Asn His Leu Gly His Phe Leu Leu Thr Asn Leu Leu Leu Asp Lys
145                 150                 155                 160

Leu Lys Ala Ser Ala Pro Ser Arg Ile Ile Asn Leu Ser Ser Leu Ala
                165                 170                 175

His Val Ala Gly His Ile Asp Phe Asp Asp Leu Asn Trp Gln Thr Arg
            180                 185                 190

Lys Tyr Asn Thr Lys Ala Ala Tyr Cys Gln Ser Lys Leu Ala Ile Val
        195                 200                 205

Leu Phe Thr Lys Glu Leu Ser Arg Arg Leu Gln Gly Ser Gly Val Thr
    210                 215                 220

Val Asn Ala Leu His Pro Gly Val Ala Arg Thr Glu Leu Gly Arg His
225                 230                 235                 240

Thr Gly Ile His Gly Ser Thr Phe Ser Ser Thr Thr Leu Gly Pro Ile
                245                 250                 255

Phe Trp Leu Leu Val Lys Ser Pro Glu Leu Val Ala Gln Pro Ser Thr
            260                 265                 270

Tyr Leu Ala Val Ala Glu Glu Leu Ala Asp Val Ser Gly Lys Tyr Phe
        275                 280                 285

Asp Gly Leu Lys Gln Lys Ala Pro Ala Pro Glu Ala Glu Asp Glu Glu
    290                 295                 300

Val Ala Arg Arg Leu Trp Ala Glu Ser Ala Arg Leu Val Gly Leu Glu
305                 310                 315                 320

Ala Pro Ser Val Arg Glu Gln Pro Leu Pro Arg
                325                 330

<210> SEQ ID NO 6
<211> LENGTH: 1699
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 21676 ADH
```

-continued

```
<220> FEATURE:
<221> NAME/KEY: CDS
<222> LOCATION: (538)...(1533)
<221> NAME/KEY: misc_feature
<222> LOCATION: (1)...(1699)
<223> OTHER INFORMATION: n = A,T,C or G

<400> SEQUENCE: 6
gcntgtgggt ccettcttna aattgggtcc ccccgtttta ggtaagttta aaagctcaag      60
gttcaaagac nggnccttttt gtcggggggct ccttgaagcc tactagatca ncggctctca   120 gcttttttt  ttgggggncc cccccctttg ggaaccccn  tggctttgct tcaaacttct     180 aaggtcttt  gtttcgttt  ctgttcctgc gccgttacag atccaagytc tgaaaaacca     240
gaaagttaac tggtaagttt agtcttttg  tcttttattt caggtcccgg atccggtggt     300
ggtgcaaatc aaagaactgc tcctcagtgg atgttgcctt tacttctagg cctgtacgaa     360
gtgttacttc tgctctaaaa gctgcggaat tctaatacga ctcactatag ggagtcgacc     420
cacgcgtccg cggacgcgtg gcggacgcg  tgggcggagc tacccaggcg gctggtgtgc     480
agcaagctcc gcgccgactc cggacgcctg acgcctgacg cctgtccccg gcccggc atg   540
                                                                Met
                                                                  1
```

| | | | | | | | | | | | | | | | |
|---|---|---|---|---|---|---|---|---|---|---|---|---|---|---|---|
| agc | cgc | tac | ctg | ctg | ccg | ctg | tcg | gcg | ctg | ggc | acg | gta | gca | ggc | gcc | 588 |
| Ser | Arg | Tyr | Leu | Leu | Pro | Leu | Ser | Ala | Leu | Gly | Thr | Val | Ala | Gly | Ala |
|  |  |  | 5 |  |  |  |  | 10 |  |  |  |  |  | 15 |  |

```
gcc gtg ctg ctc aag gac tat gtc acc ggt ggg gct tgc ccc agc aag      636
Ala Val Leu Leu Lys Asp Tyr Val Thr Gly Gly Ala Cys Pro Ser Lys
         20                  25                  30 gcc acc atc cct ggg aag acg gtc atc gtg acg ggc gcc aac aca ggc      684
Ala Thr Ile Pro Gly Lys Thr Val Ile Val Thr Gly Ala Asn Thr Gly
 35                  40                  45 atc ggg aag cag acc gcc ttg gaa ctg gcc agg aga gga ggc aac atc      732
Ile Gly Lys Gln Thr Ala Leu Glu Leu Ala Arg Arg Gly Gly Asn Ile
 50                  55                  60                  65 atc ctg gcc tgc cga gac atg gag aag tgt gag gcg gca gca aag gac      780
Ile Leu Ala Cys Arg Asp Met Glu Lys Cys Glu Ala Ala Ala Lys Asp
             70                  75                  80 atc cgc ggg gag acc ctc aat cac cat gtc aac gcc cgg cac ctg gac      828
Ile Arg Gly Glu Thr Leu Asn His His Val Asn Ala Arg His Leu Asp
         85                  90                  95 ttg gct tcc ctc aag tct atc cga gag ttt gca gca aag atc att gaa      876
Leu Ala Ser Leu Lys Ser Ile Arg Glu Phe Ala Ala Lys Ile Ile Glu
            100                 105                 110 gag gag gag cga gtg gac att cta atc aac aac gcg ggt gtg atg cgg      924
Glu Glu Glu Arg Val Asp Ile Leu Ile Asn Asn Ala Gly Val Met Arg
    115                 120                 125 tgc ccc cac tgg acc acc gag gac ggc ttc gag atg cag ttt ggc gtt      972
Cys Pro His Trp Thr Thr Glu Asp Gly Phe Glu Met Gln Phe Gly Val
130                 135                 140                 145 aac cac ctg ggt cac ttt ctc ttg aca aac ttg ctg ctg gac aag ctg     1020
Asn His Leu Gly His Phe Leu Leu Thr Asn Leu Leu Leu Asp Lys Leu
                150                 155                 160 aaa gcc tca gcc cct tcg cgg atc atc aac ctc tcg tcc ctg gcc cat     1068
Lys Ala Ser Ala Pro Ser Arg Ile Ile Asn Leu Ser Ser Leu Ala His
            165                 170                 175 gtt gct ggg cac ata gac ttt gac gac ttg aac tgg cag acg agg aag     1116
Val Ala Gly His Ile Asp Phe Asp Asp Leu Asn Trp Gln Thr Arg Lys
        180                 185                 190
```

```
tat aac acc aaa gcc gcc tac tgc cag agc aag ctc gcc atc gtc ctc      1164
Tyr Asn Thr Lys Ala Ala Tyr Cys Gln Ser Lys Leu Ala Ile Val Leu
    195                 200                 205 ttc acc aag gag ctg agc cgg cgg ctg caa ggc tct ggt gtg act gtc      1212
Phe Thr Lys Glu Leu Ser Arg Arg Leu Gln Gly Ser Gly Val Thr Val
210                 215                 220                 225 aac gcc ctg cac ccc ggc gtg gcc agg aca gag ctg ggc aga cac acg      1260
Asn Ala Leu His Pro Gly Val Ala Arg Thr Glu Leu Gly Arg His Thr
                230                 235                 240 ggc atc cat ggc tcc acc ttc tcc agc acc aca ctc ggg ccc atc ttc      1308
Gly Ile His Gly Ser Thr Phe Ser Ser Thr Thr Leu Gly Pro Ile Phe
            245                 250                 255 tgg ctg ctg gtc aag agc ccc gag ctg gtc gcc cag ccc agc aca tac      1356
Trp Leu Leu Val Lys Ser Pro Glu Leu Val Ala Gln Pro Ser Thr Tyr
        260                 265                 270 ctg gcc gtg gcg gag gaa ctg gcg gat gtt tcc gga aag tac ttc gat      1404
Leu Ala Val Ala Glu Glu Leu Ala Asp Val Ser Gly Lys Tyr Phe Asp
    275                 280                 285 gga ctc aaa cag aag gcc ccg gcc ccc gag gct gag gat gag gag gtg      1452
Gly Leu Lys Gln Lys Ala Pro Ala Pro Glu Ala Glu Asp Glu Glu Val
290                 295                 300                 305 gcc cgg agg ctt tgg gct gaa agt gcc cgc ctg gtg ggc tta gag gct      1500
Ala Arg Arg Leu Trp Ala Glu Ser Ala Arg Leu Val Gly Leu Glu Ala
                310                 315                 320 ccc tct gtg agg gag cag ccc ctc ccc aga taa cctctggagc agatttgaaa    1553
Pro Ser Val Arg Glu Gln Pro Leu Pro Arg
            325                 330 gccaggatgg cgcctccaga ccgaggacag ctgtccgcca tgcccgcagc ttcctggcac    1613
tacctgagcc gggagaccca ggactggcgg ccgctagact agtctagaga aaaaccctcc   1673
cacacctccc cctgaacctg aaacat                                         1699

<210> SEQ ID NO 7
<211> LENGTH: 418
<212> TYPE: PRT
<213> ORGANISM: Homo sapiens

<400> SEQUENCE: 7

Met Leu Pro Asn Thr Gly Arg Leu Ala Gly Cys Thr Val Phe Ile Thr
1               5                   10                  15

Gly Ala Ser Arg Gly Ile Gly Lys Ala Ile Ala Leu Lys Ala Ala Lys
            20                  25                  30

Asp Gly Ala Asn Ile Val Ile Ala Ala Lys Thr Ala Gln Pro His Pro
        35                  40                  45

Lys Leu Leu Gly Thr Ile Tyr Thr Ala Ala Glu Glu Ile Glu Ala Val
    50                  55                  60

Gly Gly Lys Ala Leu Pro Cys Ile Val Asp Val Arg Asp Glu Gln Gln
65                  70                  75                  80

Ile Ser Ala Ala Val Glu Lys Ala Ile Lys Lys Phe Gly Gly Ile Asp
                85                  90                  95

Ile Leu Val Asn Asn Ala Ser Ala Ile Ser Leu Thr Asn Thr Leu Asp
            100                 105                 110

Thr Pro Thr Lys Arg Leu Asp Leu Met Met Asn Val Asn Thr Arg Gly
        115                 120                 125

Thr Tyr Leu Ala Ser Lys Ala Cys Ile Pro Tyr Leu Lys Lys Ser Lys
    130                 135                 140

Val Ala His Ile Leu Asn Ile Ser Pro Pro Leu Asn Leu Asn Pro Val
145                 150                 155                 160
```

-continued

```
Trp Phe Lys Gln His Cys Ala Tyr Thr Ile Ala Lys Tyr Gly Met Ser
            165                 170                 175
Met Tyr Val Leu Gly Met Ala Glu Glu Phe Lys Gly Glu Ile Ala Val
        180                 185                 190
Asn Ala Leu Trp Pro Lys Thr Ala Ile His Thr Ala Ala Met Asp Met
    195                 200                 205
Leu Gly Gly Pro Gly Ile Glu Ser Gln Cys Arg Lys Val Asp Ile Ile
210                 215                 220
Ala Asp Ala Ala Tyr Ser Ile Phe Gln Lys Pro Lys Ser Phe Thr Gly
225                 230                 235                 240
Asn Phe Val Ile Asp Glu Asn Ile Leu Lys Glu Gly Ile Glu Asn
            245                 250                 255
Phe Asp Val Tyr Ala Ile Lys Pro Gly His Pro Leu Gln Pro Asp Phe
        260                 265                 270
Phe Leu Asp Glu Tyr Pro Glu Ala Val Ser Lys Lys Val Glu Ser Thr
    275                 280                 285
Gly Ala Val Pro Glu Phe Lys Glu Glu Lys Leu Gln Leu Gln Pro Lys
290                 295                 300
Pro Arg Ser Gly Ala Val Glu Glu Thr Phe Arg Ile Val Lys Asp Ser
305                 310                 315                 320
Leu Ser Asp Asp Val Val Lys Ala Thr Gln Ala Ile Tyr Leu Phe Glu
            325                 330                 335
Leu Ser Gly Glu Asp Gly Gly Thr Trp Phe Leu Asp Leu Lys Ser Lys
        340                 345                 350
Gly Gly Asn Val Gly Tyr Gly Glu Pro Ser Asp Gln Ala Asp Val Val
    355                 360                 365
Met Ser Met Thr Thr Asp Asp Phe Val Lys Met Phe Ser Gly Lys Leu
370                 375                 380
Lys Pro Thr Met Ala Phe Met Ser Gly Lys Leu Lys Ile Lys Gly Asn
385                 390                 395                 400
Met Ala Leu Ala Ile Lys Leu Glu Lys Leu Met Asn Gln Met Asn Ala
            405                 410                 415
Arg Leu
```

<210> SEQ ID NO 8
<211> LENGTH: 2535
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 21612 ADH
<220> FEATURE:
<221> NAME/KEY: CDS
<222> LOCATION: (762)...(2018)
<221> NAME/KEY: misc_feature
<222> LOCATION: (1)...(2535)
<223> OTHER INFORMATION: n = A,T,C or G

<400> SEQUENCE: 8

```
aggcagaagt atgcaaagca tgcatctcaa attagtcagc aaaccatagt cccggcccct      60
aactccgccc atcccgcccc taactccgnc ccagttccgg cccattctcc gccccatggc     120
tgactaattt ttttttattta tgcagagccg aggccgcctc ggcctctgag ctattccaga    180
agtagtgagg aggcttttttt ggaggcctag gcttttgcaa aaagctcctc gatcgagggg    240
ctcgcatctc tccttcacgc gcccgccgcc ctacctgagg ccgccatcca cgccggttga    300
gtcgcgttct gccgcctccc gcctgtggtg cctcctgaac tgcgtccgcc gtctaggtaa    360
```

-continued

```
gtttaaagct caggtcgaga ccgggccttt gtccggcgct cccttggagc ctacctagac      420
tcagccggct ctccacgctt tgcctgaccc tgcttgctca actctacgtc tttgtttcag      480
ttttctgttc tgcgccgtta cagatccaag ctctgaaaaa ccagaaagtt aactggtaag      540
tttagtcttt ttgtctttta tttcaggtcc cggatccggt ggtggtgcaa atcaaagaac      600
tgctcctcag tggatgttgc ctttacttct aggcctgtac ggaagtgtta cttctgctct      660
aaaagctgcg gaattctaat acgactcact atagggwgtc gacccacgcg tccgctcgcc      720
gccgccgctg tcgccgccac ctcctctgat ctacgaaagt c atg tta ccc aac acc      776
                                              Met Leu Pro Asn Thr
                                                1                5
```

| | | | | | | | | | | | | | | | |
|---|---|---|---|---|---|---|---|---|---|---|---|---|---|---|---|
| ggg | agg | ctg | gca | gga | tgt | aca | gtt | ttt | atc | aca | ggt | gca | agc | cgt | ggc | 824 |
| Gly | Arg | Leu | Ala | Gly | Cys | Thr | Val | Phe | Ile | Thr | Gly | Ala | Ser | Arg | Gly |
|     |     | 10  |     |     |     | 15  |     |     |     | 20  |     |     |     |     |     |

```
att ggc aaa gct att gca ttg aaa gca gca aag gat gga gca aat att      872
Ile Gly Lys Ala Ile Ala Leu Lys Ala Ala Lys Asp Gly Ala Asn Ile
         25                  30                  35 gtt att gct gca aag acc gcc cag cca cat cca aaa ctt cta ggc aca      920
Val Ile Ala Ala Lys Thr Ala Gln Pro His Pro Lys Leu Leu Gly Thr
     40                  45                  50 atc tat act gct gct gaa gaa att gaa gca gtt gga gga aag gcc ttg      968
Ile Tyr Thr Ala Ala Glu Glu Ile Glu Ala Val Gly Gly Lys Ala Leu
 55                  60                  65 cca tgt att gtt gat gtg aga gat gaa cag cag atc agt gct gca gtg     1016
Pro Cys Ile Val Asp Val Arg Asp Glu Gln Gln Ile Ser Ala Ala Val
 70                  75                  80                  85 gag aaa gcc atc aag aaa ttt gga gga att gat att ctg gta aat aat     1064
Glu Lys Ala Ile Lys Lys Phe Gly Gly Ile Asp Ile Leu Val Asn Asn
             90                  95                 100 gcc agt gcc att agt ttg acc aat aca ttg gac aca cct acc aag aga     1112
Ala Ser Ala Ile Ser Leu Thr Asn Thr Leu Asp Thr Pro Thr Lys Arg
            105                 110                 115 ttg gat ctg atg atg aac gtg aac acc aga ggc acc tac ctt gca tct     1160
Leu Asp Leu Met Met Asn Val Asn Thr Arg Gly Thr Tyr Leu Ala Ser
        120                 125                 130 aaa gca tgt att cct tat ttg aaa aag agc aaa gtt gct cat atc ctc     1208
Lys Ala Cys Ile Pro Tyr Leu Lys Lys Ser Lys Val Ala His Ile Leu
    135                 140                 145 aat atc agt cca cca ctg aac cta aat cca gtt tgg ttc aaa cag cac     1256
Asn Ile Ser Pro Pro Leu Asn Leu Asn Pro Val Trp Phe Lys Gln His
150                 155                 160                 165 tgt gct tat acc att gct aag tat ggt atg tct atg tat gtg ctt gga     1304
Cys Ala Tyr Thr Ile Ala Lys Tyr Gly Met Ser Met Tyr Val Leu Gly
                170                 175                 180 atg gca gaa gaa ttt aaa ggt gaa att gca gtc aat gca tta tgg cct     1352
Met Ala Glu Glu Phe Lys Gly Glu Ile Ala Val Asn Ala Leu Trp Pro
            185                 190                 195 aaa aca gcc ata cac act gct gct atg gat atg ctg gga gga cct ggt     1400
Lys Thr Ala Ile His Thr Ala Ala Met Asp Met Leu Gly Gly Pro Gly
        200                 205                 210 atc gaa agc cag tgt aga aaa gtt gat atc att gca gat gca gca tat     1448
Ile Glu Ser Gln Cys Arg Lys Val Asp Ile Ile Ala Asp Ala Ala Tyr
    215                 220                 225 tcc att ttc caa aag cca aaa agt ttt act ggc aac ttt gtc att gat     1496
Ser Ile Phe Gln Lys Pro Lys Ser Phe Thr Gly Asn Phe Val Ile Asp
230                 235                 240                 245 gaa aat atc tta aaa gaa gaa gga ata gaa aat ttt gac gtt tat gca     1544
Glu Asn Ile Leu Lys Glu Glu Gly Ile Glu Asn Phe Asp Val Tyr Ala
                250                 255                 260
```

-continued

```
att aaa cca ggt cat cct ttg caa cca gat ttc ttc tta gat gaa tac      1592
Ile Lys Pro Gly His Pro Leu Gln Pro Asp Phe Phe Leu Asp Glu Tyr
        265                 270                 275 cca gaa gca gtt agc aag aaa gtg gaa tca act ggt gct gtt cca gaa      1640
Pro Glu Ala Val Ser Lys Lys Val Glu Ser Thr Gly Ala Val Pro Glu
    280                 285                 290 ttc aaa gaa gag aaa ctg cag ctg caa cca aaa cca cgt tct gga gct      1688
Phe Lys Glu Glu Lys Leu Gln Leu Gln Pro Lys Pro Arg Ser Gly Ala
295                 300                 305 gtg gaa gaa aca ttt aga att gtt aag gac tct ctc agt gat gat gtt      1736
Val Glu Glu Thr Phe Arg Ile Val Lys Asp Ser Leu Ser Asp Asp Val
310                 315                 320                 325 gtt aaa gcc act caa gca atc tat ctg ttt gaa ctc tcc ggt gaa gat      1784
Val Lys Ala Thr Gln Ala Ile Tyr Leu Phe Glu Leu Ser Gly Glu Asp
            330                 335                 340 ggt ggc acg tgg ttt ctt gat ctg aaa agc aag ggt ggg aat gtc gga      1832
Gly Gly Thr Trp Phe Leu Asp Leu Lys Ser Lys Gly Gly Asn Val Gly
        345                 350                 355 tat gga gag cct tct gat cag gca gat gtg gtg atg agt atg act act      1880
Tyr Gly Glu Pro Ser Asp Gln Ala Asp Val Val Met Ser Met Thr Thr
    360                 365                 370 gat gac ttt gta aaa atg ttt tca ggg aaa cta aaa cca aca atg gca      1928
Asp Asp Phe Val Lys Met Phe Ser Gly Lys Leu Lys Pro Thr Met Ala
375                 380                 385 ttc atg tca ggg aaa ttg aag att aaa ggt aac atg gcc cta gca atc      1976
Phe Met Ser Gly Lys Leu Lys Ile Lys Gly Asn Met Ala Leu Ala Ile
390                 395                 400                 405 aaa ttg gag aag cta atg aat cag atg aat gcc aga ctg tga              2018
Lys Leu Glu Lys Leu Met Asn Gln Met Asn Ala Arg Leu
                410                 415 aggaaaatat aaaaaaaaag tcgactgcta tgctcaaaaa gtaaaaaaag ctcaacagtt    2078
aaaatctaat gtttgttttc tttcctgtta tattataagg atatgcacgt ttgttctgga   2138
aaagatagaa tttgtctcta aaagacttga aattgtaatt aaaatggcaa gctaatcaaa   2198
cataagcttc attaagtggg attctaagac agtctgtgtt tttatatttc aagggtttaa   2258 cccctttgagc cttacatctc attcactgtc tttctccaag aaaagtattt tgggcggaca  2318
gtcagatcaa gcagtaaaat tagctctttc aaatcttctt gtcatgtaaa atgaagctag  2378
tctgttttaa aatttttagt tttggattgt atactaatga aaatcttaat gatgttttkr  2438 wttttatat acytawtttw aarraaawyy twwwwwrkwc mttttwmcaa aaawtwttaa    2498
aaawkrrwww kwrytskgsg mgraswmwaw rwrammc                            2535
```

<210> SEQ ID NO 9
<211> LENGTH: 245
<212> TYPE: PRT
<213> ORGANISM: Homo sapiens

<400> SEQUENCE: 9

```
Met Gly Arg Leu Asp Gly Lys Val Ile Ile Leu Thr Ala Ala Ala Gln
1               5                   10                  15

Gly Ile Gly Gln Ala Ala Ala Leu Ala Phe Ala Arg Glu Gly Ala Lys
            20                  25                  30

Val Ile Ala Thr Asp Ile Asn Glu Ser Lys Leu Gln Glu Leu Glu Lys
        35                  40                  45

Tyr Pro Gly Ile Gln Thr Arg Val Leu Asp Val Thr Lys Lys Lys Gln
    50                  55                  60
```

-continued

```
Ile Asp Gln Phe Ala Asn Glu Val Glu Arg Leu Asp Val Leu Phe Asn
 65                  70                  75                  80

Val Ala Gly Phe Val His His Gly Thr Val Leu Asp Cys Glu Glu Lys
                 85                  90                  95

Asp Trp Asp Phe Ser Met Asn Leu Asn Val Arg Ser Met Tyr Leu Met
                100                 105                 110

Ile Lys Ala Phe Leu Pro Lys Met Leu Ala Gln Lys Ser Gly Asn Ile
            115                 120                 125

Ile Asn Met Ser Ser Val Ala Ser Ser Val Lys Gly Val Val Asn Arg
        130                 135                 140

Cys Val Tyr Ser Thr Thr Lys Ala Ala Val Ile Gly Leu Thr Lys Ser
145                 150                 155                 160

Val Ala Ala Asp Phe Ile Gln Gln Gly Ile Arg Cys Asn Cys Val Cys
                165                 170                 175

Pro Gly Thr Val Asp Thr Pro Ser Leu Gln Glu Arg Ile Gln Ala Arg
                180                 185                 190

Gly Asn Pro Glu Glu Ala Arg Asn Asp Phe Leu Lys Arg Gln Lys Thr
            195                 200                 205

Gly Arg Phe Ala Thr Ala Glu Glu Ile Ala Met Leu Cys Val Tyr Leu
210                 215                 220

Ala Ser Asp Glu Ser Ala Tyr Val Thr Gly Asn Pro Val Ile Ile Asp
225                 230                 235                 240

Gly Gly Trp Ser Leu
                245

<210> SEQ ID NO 10
<211> LENGTH: 1716
<212> TYPE: DNA
<213> ORGANISM: Homo sapiens
<220> FEATURE:
<221> NAME/KEY: misc_feature
<222> LOCATION: (0)...(0)
<223> OTHER INFORMATION: 21615 ADH
<220> FEATURE:
<221> NAME/KEY: CDS
<222> LOCATION: (637)...(1374)
<221> NAME/KEY: misc_feature
<222> LOCATION: (1)...(1716)
<223> OTHER INFORMATION: n = A,T,C or G

<400> SEQUENCE: 10
atgcaaaagc cgagnccgcc tcggcctcta agctattcca gaagtagtaa gaaggctttt    60
ttgaaggcct aggcttttgc aaaaagctcc tcgatcgagg ggctcgcatc tctccttcac   120
ggggccgccg ccctacctga ggccgccatc cacgccggtt gagtcgcgtt ctgccgcctc   180
ccgcctgtgg tgcctcctga actgcgtccg ccgtytaggt aagtttaaag ctcaggtcga   240
gaccgggcct ttgtccggcg ctcccttgga gcctacctag actcagccgg ctctccacgc   300
tttgcctgac cctgcttgct caactctacg tctttgtttc gttttctgtt ctgcgccgtt   360
acagatccaa gctctgaaaa accagaaagt taactggtaa gtttagtctt tttgtctttt   420
atttcaggtc ccggatccgg tggtggtgca aatcaaagaa ctgctcctca gtggatgttg   480
cctttacttc taggcctgta cggaagtgtt acttctgctc taaagctgc ggaattctaa    540 tacgactcac tatagggagt cgacccacgc gtccgcaaac cgagttctgg agaacgccat   600
cagctcgctg cttaaaatta aaccacaggt tccatt atg ggt cga ctt gat ggg   654
                                          Met Gly Arg Leu Asp Gly
                                            1               5
```

```
aaa gtc atc atc ctg acg gcc gct gct cag ggg att ggc caa gca gct        702
Lys Val Ile Ile Leu Thr Ala Ala Ala Gln Gly Ile Gly Gln Ala Ala
            10                  15                  20 gcc tta gct ttt gca aga gaa ggt gcc aaa gtc ata gcc aca gac att        750
Ala Leu Ala Phe Ala Arg Glu Gly Ala Lys Val Ile Ala Thr Asp Ile
        25                  30                  35 aat gag tcc aaa ctt cag gaa ctg gaa aag tac ccg ggt att caa act        798
Asn Glu Ser Lys Leu Gln Glu Leu Glu Lys Tyr Pro Gly Ile Gln Thr
    40                  45                  50 cgt gtc ctt gat gtc aca aag aag aaa caa att gat cag ttt gcc aat        846
Arg Val Leu Asp Val Thr Lys Lys Lys Gln Ile Asp Gln Phe Ala Asn
55                  60                  65                  70 gaa gtt gag aga ctt gat gtt ctc ttt aat gtt gct ggt ttt gtc cat        894
Glu Val Glu Arg Leu Asp Val Leu Phe Asn Val Ala Gly Phe Val His
                75                  80                  85 cat gga act gtc ctg gat tgt gag gag aaa gac tgg gac ttc tcg atg        942
His Gly Thr Val Leu Asp Cys Glu Glu Lys Asp Trp Asp Phe Ser Met
            90                  95                  100 aat ctc aat gtg cgc agc atg tac ctg atg atc aag gca ttc ctt cct        990
Asn Leu Asn Val Arg Ser Met Tyr Leu Met Ile Lys Ala Phe Leu Pro
        105                 110                 115 aaa atg ctt gct cag aaa tct ggc aat att atc aac atg tct tct gtg       1038
Lys Met Leu Ala Gln Lys Ser Gly Asn Ile Ile Asn Met Ser Ser Val
    120                 125                 130 gct tcc agc gtc aaa gga gtt gtg aac aga tgt gtg tac agc aca acc       1086
Ala Ser Ser Val Lys Gly Val Val Asn Arg Cys Val Tyr Ser Thr Thr
135                 140                 145                 150 aag gca gcc gtg att ggc ctc aca aaa tct gtg gct gca gat ttc atc       1134
Lys Ala Ala Val Ile Gly Leu Thr Lys Ser Val Ala Ala Asp Phe Ile
                155                 160                 165 cag cag ggc atc agg tgc aac tgt gtg tgc cca gga aca gtt gat acg       1182
Gln Gln Gly Ile Arg Cys Asn Cys Val Cys Pro Gly Thr Val Asp Thr
            170                 175                 180 cca tct cta caa gaa aga ata caa gcc aga gga aat cct gaa gag gca       1230
Pro Ser Leu Gln Glu Arg Ile Gln Ala Arg Gly Asn Pro Glu Glu Ala
        185                 190                 195 cgg aat gat ttc ctg aag aga caa aag acg gga aga ttc gca act gca       1278
Arg Asn Asp Phe Leu Lys Arg Gln Lys Thr Gly Arg Phe Ala Thr Ala
    200                 205                 210 gaa gaa ata gcc atg ctc tgc gtg tat ttg gct tct gat gaa tct gct       1326
Glu Glu Ile Ala Met Leu Cys Val Tyr Leu Ala Ser Asp Glu Ser Ala
215                 220                 225                 230 tat gta act ggt aac cct gtc atc att gat gga ggc tgg agc ttg tga       1374
Tyr Val Thr Gly Asn Pro Val Ile Ile Asp Gly Gly Trp Ser Leu
                235                 240                 245 ttttaggatc tccatggtgg gaaggaaggc aggcccttcc tatccacagt gaacctggtt     1434
acgaagaaaa ctcaccaatc atctccttcc tgttaatcac atgttaatga aaataagctc     1494
tttttaatga tgtcactgtt tgcaagagtc tgattcttta agtatattaa tctctttgta     1554
atctcttctg aaatcattgt aaagaaataa aaatattgaa ctcaaaaaaa aaaaaaaaa      1614 aagggcggcc gctagactag tctagagaaa aaacctccca cacctccccc tgaacctgaa     1674
acataaaatg aatgcmattg ttgktggtaa cttgttattg ca                        1716
```